United States Patent
Zhang

(10) Patent No.: US 10,078,043 B2
(45) Date of Patent: Sep. 18, 2018

(54) METHOD AND SYSTEM FOR EXHAUST PARTICULATE MATTER SENSING

(71) Applicant: Ford Global Technologies, LLC, Dearborn, MI (US)

(72) Inventor: Xiaogang Zhang, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 262 days.

(21) Appl. No.: 15/063,703

(22) Filed: Mar. 8, 2016

(65) Prior Publication Data

US 2017/0261417 A1    Sep. 14, 2017

(51) Int. Cl.
*G01N 15/06*    (2006.01)
*G01M 15/10*    (2006.01)
*G01N 15/00*    (2006.01)

(52) U.S. Cl.
CPC ...... *G01N 15/0656* (2013.01); *G01M 15/102* (2013.01); *G01N 2015/0046* (2013.01)

(58) Field of Classification Search
CPC ............ G01M 15/102; G01N 15/0656; G01N 2015/0046
See application file for complete search history.

(56) References Cited

U.S. PATENT DOCUMENTS

| | | | |
|---|---|---|---|
| 2011/0062973 A1* | 3/2011 | Paterson | F02D 41/1466 324/693 |
| 2011/0232268 A1* | 9/2011 | Nelson | G01N 15/0656 60/276 |
| 2011/0314796 A1* | 12/2011 | Nakamura | F01N 9/002 60/276 |
| 2012/0144813 A1* | 6/2012 | Yahata | F01N 11/007 60/311 |
| 2015/0355066 A1 | 12/2015 | Zhang | |
| 2015/0355067 A1 | 12/2015 | Zhang et al. | |
| 2016/0320285 A1* | 11/2016 | Weber | G01N 15/0656 |
| 2017/0130636 A1* | 5/2017 | Bilby | F01N 3/023 |

FOREIGN PATENT DOCUMENTS

WO    2006027287 A1    3/2006

OTHER PUBLICATIONS

Kubinski, David John, "Method and System for Exhaust Particulate Matter Sensing," U.S. Appl. No. 14/613,012, filed Feb. 3, 2015, 56 pages.
Yi, Jianwen James et al., "Systems and Methods for Sensing Particulate Matter," U.S. Appl. No. 14/842,573, filed Sep. 1, 2015, 41 pages.

\* cited by examiner

*Primary Examiner* — Francis C Gray
(74) *Attorney, Agent, or Firm* — Julia Voutyras; McCoy Russell LLP

(57) ABSTRACT

Methods and systems are provided for a particulate matter sensor positioned downstream of a diesel particulate filter in an exhaust system. In one example, a particulate matter sensor may include an outer non-perforated tube including a plurality of negative electrodes formed along the inner surface, a guiding tube including a perforated central element and an inner tube, the central element including a plurality of positive electrodes formed along the outer surface. By forming the electrodes on different cylindrical surfaces, and separating the electrodes by a gap, a more uniform electric field may be generated in the gap between the electrodes, thereby boosting soot capture and increasing particulate matter sensor sensitivity.

20 Claims, 10 Drawing Sheets

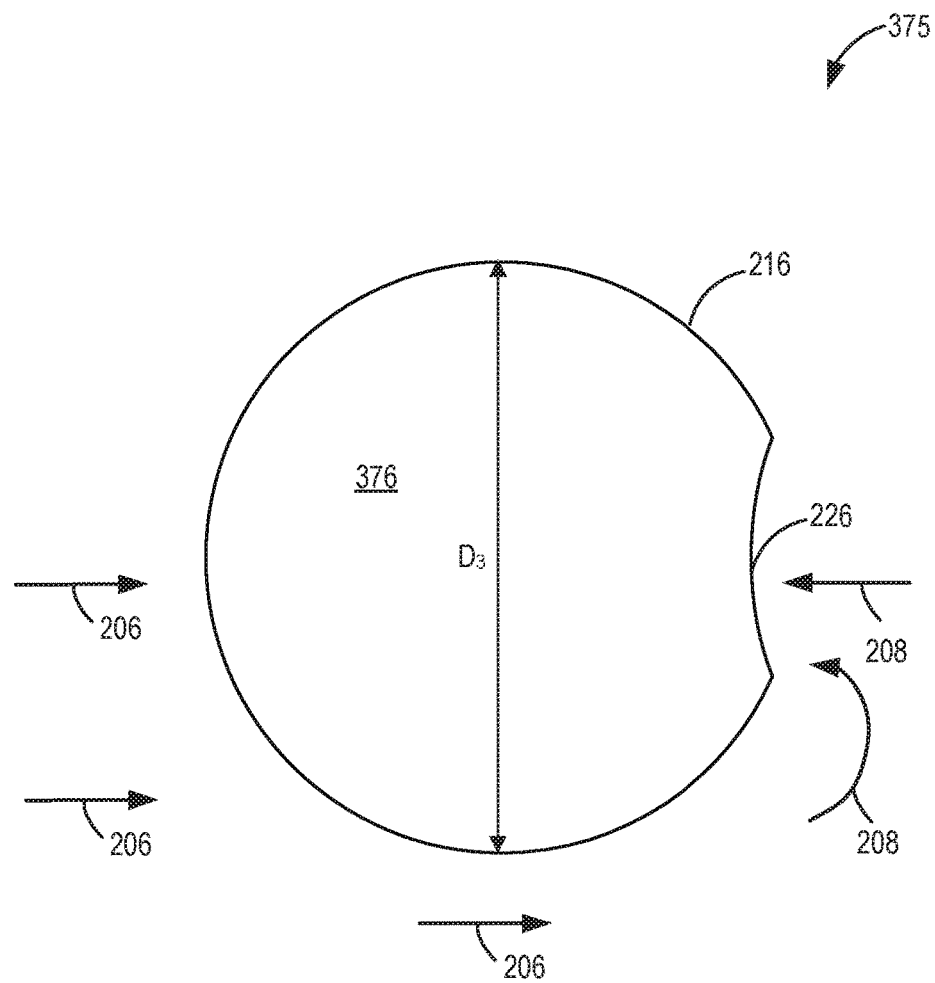
FIG. 3C
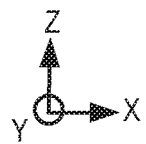

METHOD AND SYSTEM FOR EXHAUST PARTICULATE MATTER SENSING

FIELD

The present description relates generally to the design and use of resistive-type particle matter (PM) sensors in an exhaust gas flow.

BACKGROUND/SUMMARY

Diesel combustion may generate emissions, including particulate matter (PM). The particulate matter may include diesel soot and aerosols such as ash particulates, metallic abrasion particles, sulfates, and silicates. When released into the atmosphere, PM can take the form of individual particles or chain aggregates, with most in the invisible sub-micrometer range of 100 nanometers. Various technologies have been developed for identifying and filtering out exhaust PMs before the exhaust is released to the atmosphere.

As an example, PM or soot sensors may be used in vehicles having internal combustion engines. A PM sensor may be located upstream and/or downstream of a diesel particulate filter (DPF), and may be used to sense PM loading on the filter and diagnose operation of the DPF. Resistive PM sensors typically include planar interdigitated electrodes that sense a PM or soot load based on a correlation between a measured change in electrical conductivity between a pair of electrodes and the amount of PM deposited between the measuring electrodes. Specifically, the interdigitated electrodes are formed on a common substrate, and the measured conductivity across the electrodes provides a measure of soot accumulation. As such, the electrostatic fields in the planar electrodes are stronger near the surface of the electrodes, and occur tangential to the electrode surface. In addition, the electrostatic fields decay rapidly at distances away from the electrode surface. As a result, soot particles flowing close to the surface of the electrode experiences sufficient electrostatic forces to be trapped onto the electrode surface, while other soot particles may escape. This can lead to poor soot capture and distribution. Further, due to the planar geometry of the sensing electrodes, soot may be accumulated just along one surface (the surface including the electrodes, for example). Consequently, most of the soot in the exhaust stream may go undetected, leading to reduced sensor sensitivity.

One example PM sensor design is shown by Heimann et al. in WO 2006027287. Therein, the interdigitated electrodes are distributed radially around a cylindrical surface thereby increasing the surface area for soot adsorption, and further increasing sensor sensitivity.

However, the inventors herein have recognized potential issues with such an approach. The interdigitated electrodes formed on the cylindrical surface described by Heinmann et al. may continue to have reduced soot capture due to the poor electrostatic attraction experienced by the soot particles located away from the sensor surface. In particular, even with the cylindrical surface, the electrostatic field generated between the electrodes remains tangential to the surface of the sensor. Consequently, the soot particles may experience stronger electrostatic attraction when they are closer to the sensor surface, while other soot particles may continue to escape undetected by the sensor. Further, the sensor output may be affected by the presence of contaminants and/or water droplets impinging on the sensor surface.

The inventors have identified an approach to at least partly address these issues while improving the sensitivity of the PM sensor. In one example approach, PM sensor reliability may be increased by a particulate matter sensor comprising an outer, non-perforated tube with a plurality of negative electrodes along an inner surface, a central, perforated element with a plurality of positive electrodes along an outer surface of the central element, the central element positioned within the outer tube, and an inner tube appended to the central element, each of the outer tube, the central element, and the inner tube having a common axis. In this way, by forming the positive and negative electrodes on different surfaces separated by a gap, the electrostatic fields may be generated normal to each of the surfaces, and may be more uniform in the gap between the electrode surfaces. Thus, soot distribution and accumulation across the electrodes of the sensor may be more uniform.

As one example, an exhaust PM sensor may be configured with sensor electrodes and may be positioned downstream of a particulate filter in an exhaust pipe. The PM sensor may include an outer cylindrical protection tube and an inner guiding tube. The outer tube may protect the sensor electrodes while the guiding tube may guide the exhaust gas towards the sensor electrodes positioned within the outer tube. The guiding tube may include a smaller inner cylindrical non-perforated tube coupled to a larger hollow central element. The inner tube may further trap larger particulates and water droplets in the exhaust stream at an inlet of the inner tube, thereby stopping them from impinging on the sensor electrodes. The central element may include a plurality of perforations through which exhaust gas may be released from the inner tube into a gap formed between the central element and the outer tube. In one example, the central element may be an extension of the inner tube, extending towards a center of the outer tube, and may be positioned centrally within the outer tube.

Sensor electrodes may include a plurality of positive electrodes and a plurality of negative electrodes formed on different surfaces of the central element and the outer tube and may be separated from each other by the gap. Specifically, the negative electrodes may be formed on an inner surface of the outer tube, while the positive electrodes may be formed on an outer surface of the central element. The exhaust entering the PM sensor via the inlet may be directed towards the perforated central element. The exhaust may then flow through the perforations of the central element into the gap separating the sensor electrodes. Soot particles in the exhaust may experience a uniform electric field in the gap due to the separation of the plurality of positive electrodes from the plurality of negative electrodes. As a result, the particles may be evenly deposited in the gap between formed between the sensor electrodes. Sensor regeneration may be initiated once a sufficient amount of soot has been accumulated in the gap.

In this way, by positioning positive and negative electrodes of a PM sensor on surfaces of distinct members of the sensor assembly, and by separating the positive and negative electrodes by the gap, an electrostatic field may be generated across the gap that is normal to each of the electrode surfaces. The technical effect of separating the electrodes and generating electrostatic fields that are normal in the gap between the electrodes is that the electrostatic field generated in the gap may be rendered more uniform. As a result, soot in the exhaust stream may be deposited more uniformly across the electrode surfaces. In addition, by generating electrostatic fields across the gap, electrostatic field does not decay in the gap between the sensor electrodes and hence all soot particles in the gap experience substantially similar electrostatic field. Overall, these characteristics of the sensor assembly may improve the accuracy and reliability of the PM sensor. As such, this increases the accuracy of particulate matter load estimation on a particulate matter filter. In addition, PM sensor sensitivity fluctuations due to impingement of large particulates on the sensing electrodes may be reduced. By enabling more accurate diagnosis of an exhaust DPF, exhaust emissions compliance may be increased.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 3A-3C show cross-sectional views of an outer tube, a perforated region, and a non-perforated region of a guiding tube of the PM sensor.

DETAILED DESCRIPTION

Figure 1:
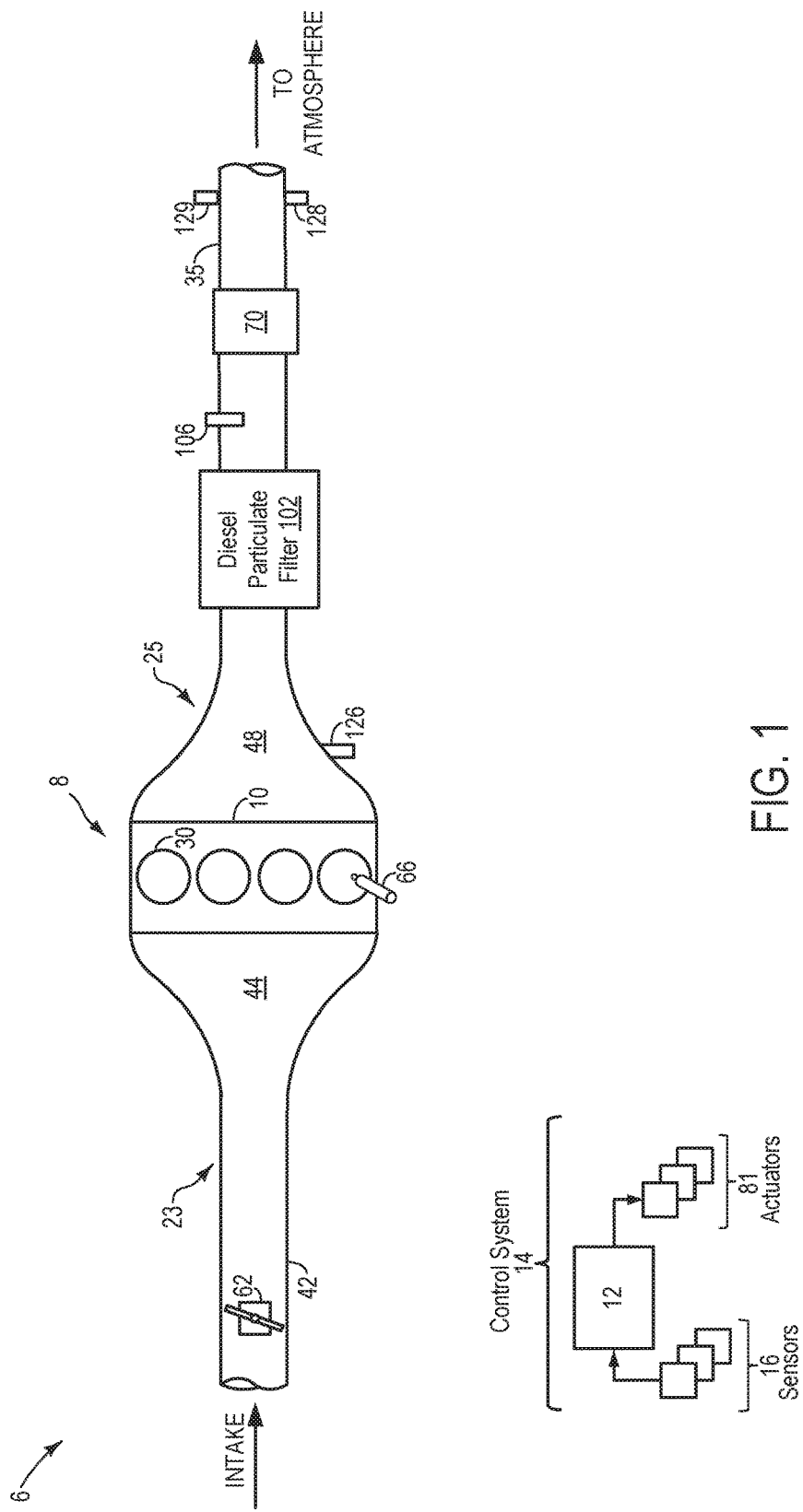
FIG. 1 shows a schematic diagram of an engine and an associated particulate matter (PM) sensor positioned in an exhaust flow.
Figure 3A:
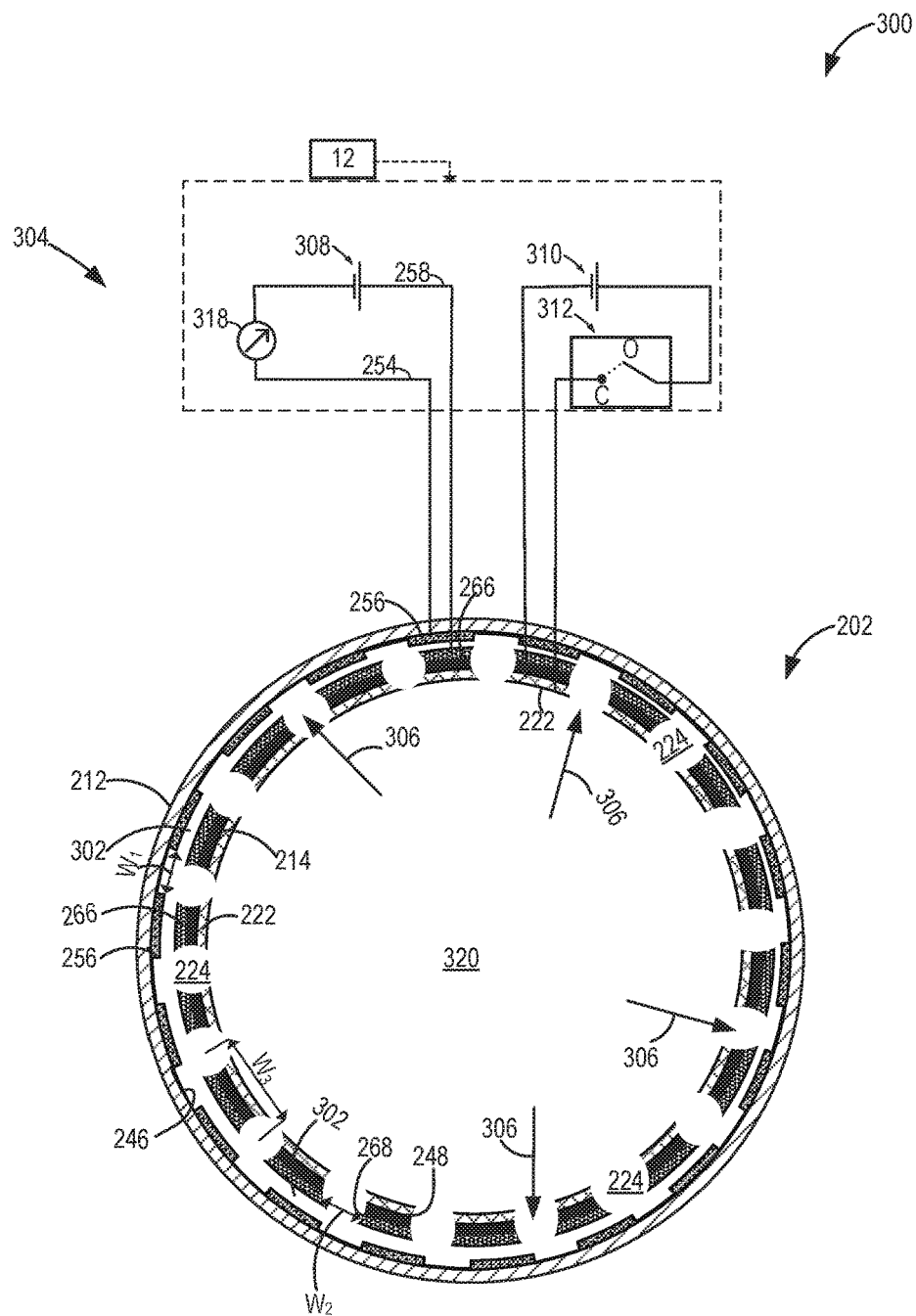
Figure 3B:
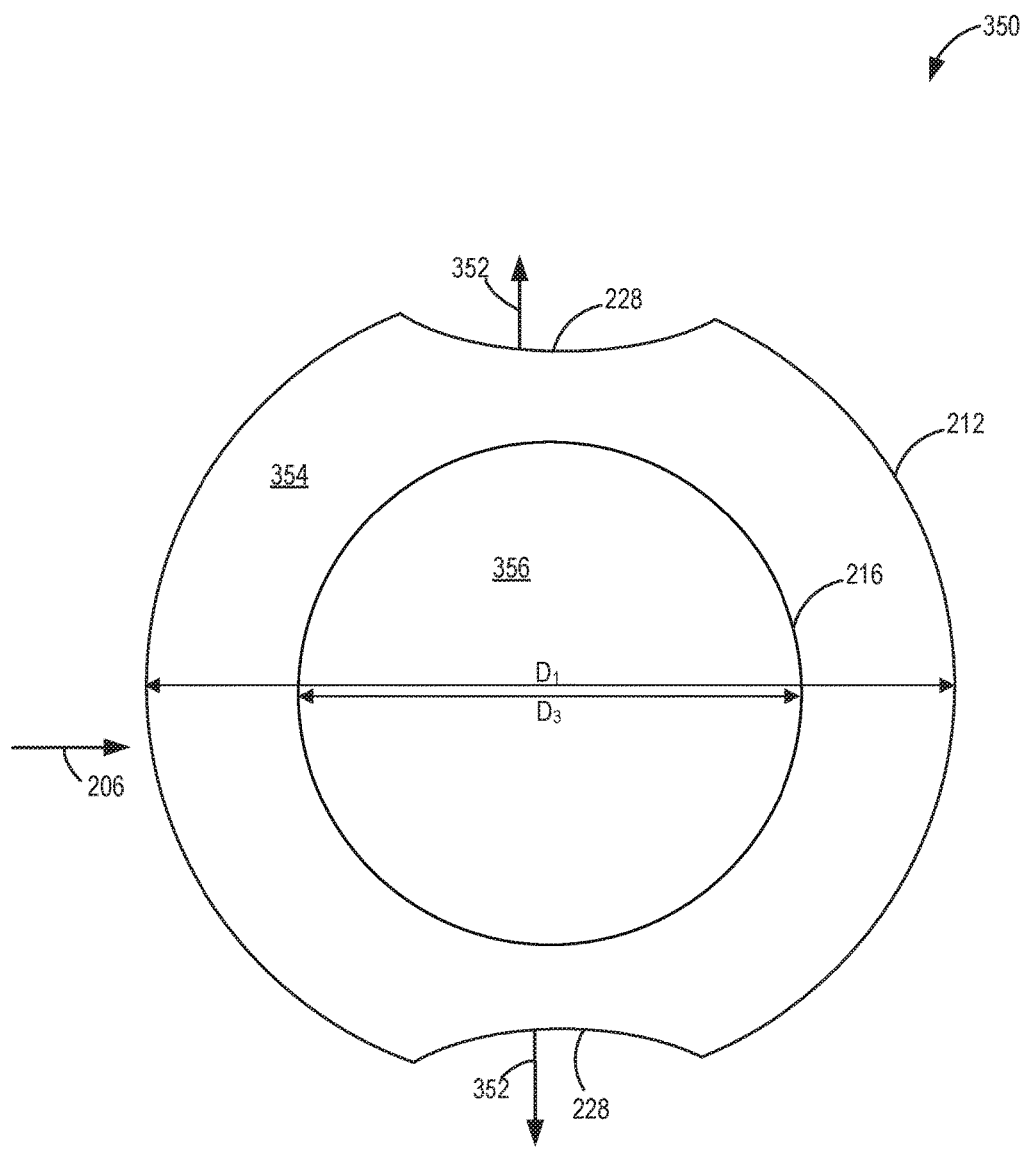
Figure 4:
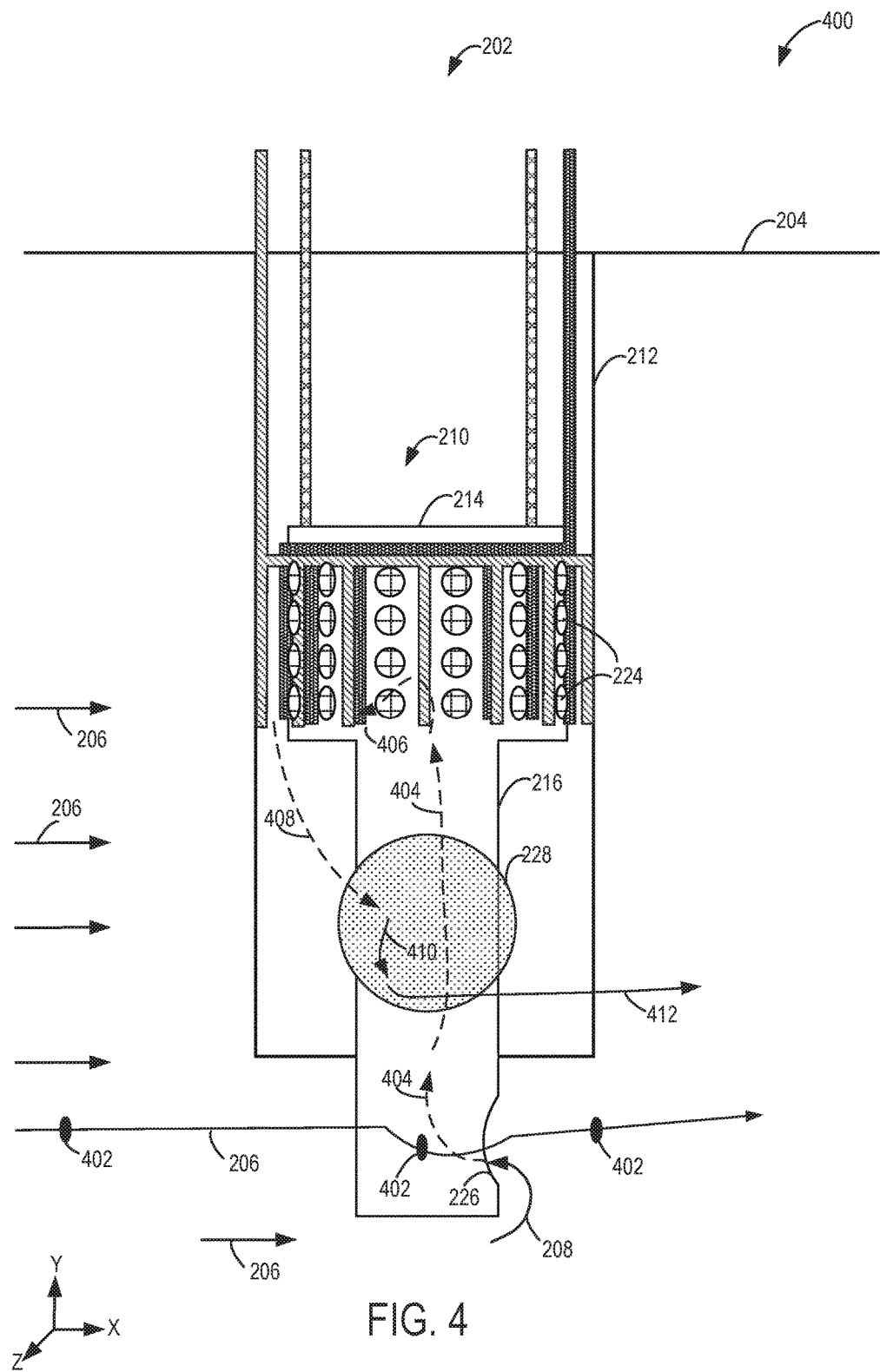
FIG. 4 shows a schematic diagram of the PM sensor showing exhaust flowing into the guiding tube and out of the outer tube of the PM sensor.

The following description relates to systems and methods for measuring the amount of particulate matter stored on an engine exhaust particulate filter, such as in the vehicle system of FIG. 1. A cylindrical particulate matter (PM) sensor configured with positive and negative electrodes distributed on different surfaces of distinct sensor elements and further separated by a gap (FIG. 2) may be located downstream of the exhaust particulate filter. The negative electrodes may be formed on an inner surface of an outer, non-perforated tube of the PM sensor and the positive electrodes may be formed on an outer surface of a perforated region of a guiding tube of the PM sensor. Thus, the electrodes are formed on separate cylindrical surfaces, and further separated by the gap. The guiding tube may further include a smaller non-perforated region coupled to the perforated region, both of which are positioned coaxially within the outer tube. Cross-sectional views of the outer tube, the perforated region, and non-perforated region of the guiding tube are shown in FIGS. 3A-3C. The guiding tube and the outer tubes may include inlet and outlet holes respectively configured to direct an exhaust into and out of the PM sensor as shown in FIG. 4. A plurality of perforations on the guiding tube may direct exhaust into the gap between the electrodes where particulates in the exhaust may be trapped and accumulated. A controller may be configured to perform a control routine, such as the example routine of FIG. 5, to accumulate particulates in the gap between the positive and the negative electrodes. Further, the controller may intermittently clean the PM sensor (FIG. 6) to enable continued PM monitoring. The controller may also be configured to perform a routine, such as the example routine of FIG. 7, to regenerate the exhaust particulate filter based on a time between PM sensor regenerations. An example of filter diagnostics is shown in FIG. 8. In this way, PM sensor sensitivity may be increased.

FIG. 1 shows a schematic depiction of a vehicle system 6. The vehicle system 6 includes an engine system 8. The engine system 8 may include an engine 10 having a plurality of cylinders 30. Engine 10 includes an engine intake 23 and an engine exhaust 25. Engine intake 23 includes a throttle 62 fluidly coupled to the engine intake manifold 44 via an intake passage 42. The engine exhaust 25 includes an exhaust manifold 48 eventually leading to an exhaust passage 35 that routes exhaust gas to the atmosphere. Throttle 62 may be located in intake passage 42 downstream of a boosting device, such as a turbocharger (not shown), and upstream of an after-cooler (not shown). When included, the after-cooler may be configured to reduce the temperature of intake air compressed by the boosting device.

Engine exhaust 25 may include one or more emission control devices 70, which may be mounted in a close-coupled position in the exhaust. One or more emission control devices may include a three-way catalyst, lean NOx filter, SCR catalyst, etc. Engine exhaust 25 may also include diesel particulate filter (DPF) 102, which temporarily filters PMs from entering gases, positioned upstream of emission control device 70. In one example, as depicted, DPF 102 is a diesel particulate matter retaining system. DPF 102 may have a monolith structure made of, for example, cordierite or silicon carbide, with a plurality of channels inside for filtering particulate matter from diesel exhaust gas. Tailpipe exhaust gas that has been filtered of PM, following passage through DPF 102, may be measured in a PM sensor 106 and further processed in emission control device 70 and expelled to the atmosphere via exhaust passage 35. In the depicted example, PM sensor 106 is a resistive sensor that estimates the filtering efficiency of the DPF 102 based on a change in conductivity measured across the electrodes of the PM sensor. A schematic view 200 of the PM sensor 106 is shown at FIG. 2, as described in further detail below.

The vehicle system 6 may further include control system 14. Control system 14 is shown receiving information from a plurality of sensors 16 (various examples of which are described herein) and sending control signals to a plurality of actuators 81 (various examples of which are described herein). As one example, sensors 16 may include exhaust flow rate sensor 126 configured to measure a flow rate of exhaust gas through the exhaust passage 35, exhaust gas sensor (located in exhaust manifold 48), temperature sensor 128, pressure sensor 129 (located downstream of emission control device 70), and PM sensor 106. Other sensors such as additional pressure, temperature, air/fuel ratio, exhaust flow rate and composition sensors may be coupled to various locations in the vehicle system 6. As another example, the actuators may include fuel injectors 66, throttle 62, DPF valves that control filter regeneration (not shown), switch of electric circuit, etc. The control system 14 may include a controller 12. The controller 12 may be configured with computer readable instructions stored on non-transitory memory. The controller 12 receives signals from the various sensors of FIG. 1, processes the signals, and employs the various actuators of FIG. 1 to adjust engine operation based on the received signals and instructions stored on a memory of the controller. For example, during PM sensor regeneration, the controller may close the switch in the electric circuit for a threshold time to apply a certain voltage to heating elements coupled to the PM sensor to heat the sensor electrodes and burn off soot particles deposited on the PM sensor electrodes. Example routines are described herein with reference to FIGS. 5-7.

Figure 2:
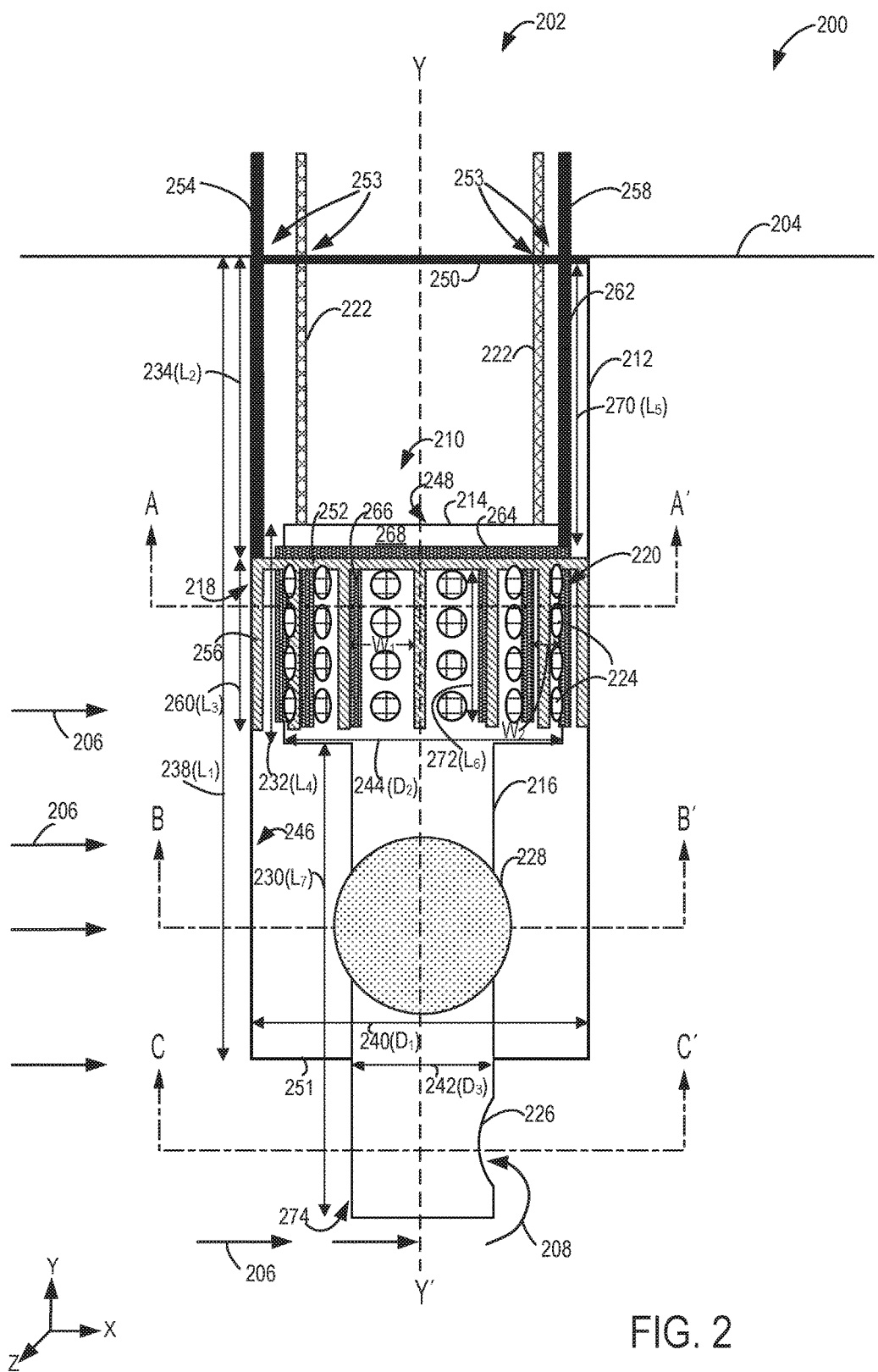
FIG. 2 shows a schematic diagram of the PM sensor.

Turning now to FIG. 2, schematic view 200 of an example embodiment of a particulate matter (PM) sensor 202 (such as PM sensor 106 of FIG. 1) is shown. The PM sensor 202 may be configured to measure PM mass and/or concentration in the exhaust gas, and as such, may be coupled to an exhaust passage (e.g., such as the exhaust passage 35 shown in FIG. 1), upstream or downstream of a diesel particulate filter (such as DPF 102 shown in FIG. 1).

FIG. 2 shows example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with a space there-between and no other components may be referred to as such, in at least one example.

In the schematic view 200, the PM sensor 202 is disposed inside an exhaust passage 204, downstream of a diesel particulate filter. Exhaust gases are shown flowing (along X-axis) from downstream of the diesel particulate filter towards an exhaust tailpipe, via the PM sensor, as indicated by arrows 206. PM sensor 202 includes an outer, protection tube 212 and an inner guiding tube 210. The outer tube 212 may be a non-perforated hollow cylindrical tube, and the guiding tube 210 may be positioned coaxially within the outer tube 212. Specifically, the outer tube 212 and the guiding tube 210 may share a common central axis Y-Y'. The guiding tube 210 may be an inner hollow tube positioned inside the outer tube 212 and held to the outer tube 212 by screws (not shown) located along the surface of the outer tube, for example. In some examples, the outer tube 212 may also be referred to as a first cylindrical element, and the guiding tube 210 may be referred to as a second cylindrical element. Herein, the second cylindrical element is positioned coaxially within the first cylindrical element.

The outer tube 212 may be a cylindrical tube with a diameter $D_1$ (arrow 240) and may be mounted to the exhaust passage 204 via a sensor boss (not shown). The outer tube 212 may include insets 253 on a top surface 250 through which electrical connections (such as 254, 258 and 222) may be inserted into the outer tube 212. As such, the top surface 250 of the outer tube 212 seals the tube to protect the sensor electrodes housed within the PM sensor 202. The outer tube 212 may be mounted onto the exhaust passage 204 such that a central axis Y-Y' of the outer tube 212 is along the Y-axis. Specifically, the central axis Y-Y' of the outer tube 212 is orthogonal to a direction of exhaust flow (arrow 206) in the exhaust passage 204.

The outer tube 212 extends into a portion inside the exhaust passage 204. Herein, the outer tube 212 extends to a length $L_1$ (arrow 238) into the exhaust passage 204. The depth to which the outer tube extends into the exhaust passage may depend on the diameter of the exhaust passage.

In some examples, the outer tube may extend to about one third to two third of the exhaust pipe diameter.

The inner guiding tube 210 of the PM sensor 202 is positioned coaxially within the outer tube 212. The guiding tube 210 may include a larger perforated portion/region 214 appended to a smaller non-perforated portion/region 216. The perforated portion 214 (herein also referred to as central element) is configured as a hollow cylindrical tube of length $L_4$ (arrow 232) and diameter $D_2$ (arrow 244). The non-perforated portion 216 (herein also referred to as an inner tube) is a hollow cylindrical tube of length $L_7$ (arrow 230) and diameter $D_3$ (arrow 242). Herein, the diameter $D_2$ of the central element 214 may be larger than the diameter $D_3$ of the inner tube 216. Thus, the inner tube may be smaller than each of the central element, and the outer tube ($D_3<D_2<D_1$, for example).

As an example, the guiding tube 210 may be manufactured as a single piece including both the larger perforated portion and the smaller non-perforated portion and the single piece may be positioned coaxially within the outer tube. The guiding tube may alternatively be referred to as an inner tube, including both the perforated and the non-perforated region. As another example, the smaller non-perforated portion and the larger perforated portion may be manufactured separately, and then coupled together to form the guiding tube 210.

In the depicted example, the length $L_4$ of the central element 214 is smaller than the length $L_7$ of the inner tube 216. In other examples, the length $L_4$ of the central element 214 may be longer than the length $L_7$ of the inner tube 216. In still other examples, the central element 214 and the inner tube 216 may be of substantially equal length. However, the lengths of each of the central element 214, the inner tube 216, and the outer tube 212 may be selected such that a portion 274 of the inner tube 216 extends beyond a bottom surface 251 of the outer tube 212 into the exhaust passage 204. Further, the bottom surface 251 of the outer tube may include a cutout through which a portion 274 of the inner tube 216 extends into the exhaust passage 204. As such, the diameter of the cutout may be substantially equal to the diameter $D_3$ of the inner tube 216. Furthermore, the bottom surface 251 may be sealed. Thus, exhaust gas may not enter the PM sensor 202 via the bottom surface 251 of the outer tube 212. However, the exhaust gas may enter the PM sensor 202 via an inlet 226 located on the inner tube 216 and the exhaust gas may exit via outlet holes (herein also referred to as exit apertures) 228 located on the outer tube 212, as will be described in detail with reference to FIGS. 3A-3C and 4.

Turning now to FIG. 3C, a cross-sectional view 375 of the PM sensor 202 in a plane along line C-C' of FIG. 2 is shown. Herein, a cross-section of the inner tube 216 of the PM sensor extending into the exhaust pipe is shown. As described earlier, the inner tube 216 may be a hollow cylindrical tube with a diameter $D_3$. The inner tube 216 may include an inlet 226 positioned such that a portion of the exhaust gas enters the inner tube 216 via the inlet 226 in a direction indicated by arrow 208. Specifically, the direction of exhaust flow into inner tube 216 via the inlet 226 may be opposite to the direction of exhaust flow in the exhaust pipe (indicated by arrow 206). In one example, the inlet 226 may be configured as a hole cutout from the inner tube 216. Various other geometries of the inlet 226 may be possible without deviating from the scope of the disclosure. Other example geometries include slits, apertures, and the like.

The inlet 226 is engineered along a surface of the inner tube 216 that is closer to the exhaust tail pipe, and is located further away from the particulate filter positioned upstream of the PM sensor, for example. As such, a pressure difference may occur at and near the inlet 226 that may allow a larger portion of the exhaust to enter the inner tube 216.

Exhaust entering the inner tube 216 may be contained within region 376 of the inner tube. Exhaust gas then travels up the length of the inner tube 216 and towards the central element 214 (FIG. 2), for example. Returning to FIG. 2, a bottom surface of the inner tube 216 may be sealed. Thus, exhaust gas may enter the PM sensor 202 via the inlet 226 located on the inner tube 216 and not via the bottom surface of the inner or the outer tube, for example. Exhaust entering the PM sensor via the inlet 226 travels the length of the inner tube (e.g., a distance of $L_7$ inside the inner tube 216) and then flows into the central element 214.

As explained earlier, the central element 214 may be a hollow cylinder of length $L_4$ (arrow 232) positioned within the outer tube 212 such that a central axis of the central element 214 coincides with the central axis of each of the outer tube 212 and the inner tube 216. Specifically, the central axis of the central element 214 coincides with the central axis Y-Y' of the outer tube 212. As such, the central element 214 may be coupled to the inner tube 216. The central element 214 may be coupled to an end of the inner tube 216 that is further away from the inlet 226 and closer to the top surface 250 of the outer tube 212, for example. The hollow central element 214 may further include a plurality of perforations 224 distributed along the surface. Further, the plurality of perforations on the central element 214 extend through a thickness of the central element. In one example, the plurality of perforations 224 may be holes that are circular in shape and evenly spaced along the surface of the central element 214. As such, the perforations may extend from each of an outer surface 268 and an inner surface of the central element 214. Various geometries and spacing of the perforations may be possible, including but not limited to cylindrical geometries, spherical geometries, V-shaped geometries, and the like. As such, exhaust flowing into the PM sensor via the inlet 226 on the inner tube may flow towards the central element 214, and exit the central element via the perforations 224. In one example, a top surface of the central element may be sealed to block exhaust gas from escaping through the top of the PM sensor. Thus, exhaust may only exit the central element via the perforations.

The central element 214 is smaller in diameter than the outer tube 212, and hence when placed inside the outer tube 212, the central element 214 is separated from the outer tube 212 by a gap. As such, the gap may be based on a difference in diameters of the outer tube 212 and the central element 214, ($D_1$-$D_2$, for example).

Exhaust exiting the central element 214 via the perforations 224 may be released into the space/gap between the central element 214 and the outer tube 212. Herein, the exhaust gas may encounter sensor electrodes formed on surfaces of each of the outer tube and the central element. The geometry and positioning of the sensor electrodes will be explained in detail below.

Traditional PM sensors include interdigitated electrodes formed on a common planar substrate that is positioned within the outer protection tube. Typically, the outer tube of the PM sensor serves to protect sensor electrodes positioned there within. Since the sensor electrodes are interdigitated along the substrate, the electrostatic fields generated between the sensor electrodes are along the planar surface and restricted to regions closer to the surface of the electrodes. As a result, particulates flowing close to the electrode surface may experience the electrostatic pull, and get deposited on the electrode surface. However, particulates that are further away from the electrode surface may experience a weak electrostatic pull, and may not get accumulated on the electrode surface, the particulates then escaping into the atmosphere undetected.

The inventors herein recognized that it may be possible to generate stronger and more uniform electric fields between the sensor electrodes by forming the electrodes on different surfaces of different sensor elements (or distinct sensor structures), without adding additional components to the PM sensor. For example, an inner surface 246 of the outer tube 212 may include a plurality of electrodes 218. Similarly, an outer surface 268 of the central element 214 may include a plurality of electrodes 220. The plurality of electrodes 218 and 220 may be distributed such that the electrodes are facing each other and further separated from each other by the gap. Herein, the gap may not include any components. By connecting the electrodes to positive and negative terminals of a voltage supply, a uniform electrostatic field may be generated in the gap between the electrodes.

Exhaust exiting the central element 214 via the plurality of perforations 224 may enter into the gap between the outer tube 212 and the central element 214. By including electrodes across the gap, particulates in the exhaust stream may be trapped onto the electrodes and in the gap between the electrodes by the uniform electric field generated in the gap, for example. Herein, the soot particles accumulate in the gap between the electrodes forming soot bridges.

To elucidate further, the plurality of electrodes 218 may be connected to a negative terminal of a voltage supply and hereafter interchangeably referred to as plurality of negative electrodes 218. Similarly, the plurality of electrodes 220 may be connected to a positive terminal of the voltage supply and referred to as plurality of positive electrodes 220. In some example embodiments, the polarity of the electrodes 218 and 220 may be interchanged. The electrodes are typically manufactured from metals such as platinum, gold, osmium, rhodium, iridium, ruthenium, aluminum, titanium, zirconium, and the like, as well as, oxides, cements, alloys and combination comprising at least one of the foregoing metals.

In one example, the outer tube 212 and the central element 214 may be manufactured from highly insulating materials. Possible electrically insulating materials may include oxides such as alumina, zirconia, yttria, lanthanum oxide, silica, and combinations comprising at least one of the foregoing, or any like material capable of inhibiting electrical communication. The plurality of negative electrodes 218 and the plurality of positive electrodes 220 may be directly formed on the inner surface of the outer tube 212 and the outer surface of the central element 214 respectively.

Turning the focus to the plurality of negative electrodes 218, the plurality of negative electrodes 218 are formed directly on the inner surface 246 of the outer tube 212, and hence may be in face-sharing contact with the inner surface 246 of the outer tube 212. The plurality of negative electrodes 218 may include a first portion 252, and a second portion 256, both of which are formed along the inner surface 246 of the outer tube 212. Herein, the first portion 252 is an unbranched region and the second portion 256 includes a plurality of "tines" branching off at locations along the first portion 252. An electrical wire 254 may connect each of the first portion 252 and the second portion 256 to a negative terminal of a voltage supply located outside outer tube 212. As such, a portion of the electrical wire 254 may be housed inside the outer tube 212 and the remainder may be housed outside the exhaust passage 204 (as one example, <1 meter away), and electrically coupled to the voltage supply and a measurement device which will be explained later with reference to FIG. 3A.

The second portion 256 of the negative electrode 218 may begin at a length $L_2$ (arrow 234) from the top surface 250 of the outer tube 212. The length $L_2$ may be determined based on the length $L_1$ of the outer tube 212 inside the exhaust passage 204. As an example, the length $L_2$ may be one-third of length $L_1$. The second portion 256 may include a plurality of tines, each tine of length $L_3$ (arrow 260) formed at a first spacing ($W_1$) along the inner surface 246 of the outer tube 212. The spacing $W_1$ may typically be in the range from 10 micrometers to 100 micrometers with a linewidth of each individual electrode being about the same value, although the latter is not necessary. The second portion 256 may be evenly spaced and substantially parallel to the Y-axis. Said another way, the plurality of tines of the second portion 256 may be perpendicular to the direction of flow of exhaust (arrow 206) in the exhaust passage 204.

The first portion 252 of the negative electrode 218 may be formed along an inner circumference of the outer tube. As such, the first portion 252 may begin at the length $L_2$ (arrow 234) from the top surface 250 of the outer tube 212 and may be formed along the inner surface of 246 of the outer tube 212. The first portion 252 may include a curvature and as such, the curvature may be substantially equal to the curvature of the outer tube 212. In effect, a length of the first portion 252 may be substantially equal to the inner circumference of the outer tube 212. Further, the plurality of tines of the second portion 256 may be electrically coupled to the first portion 252. For example, a first tine (herein also referred to as a first of the plurality of negative electrodes) may begin at length $L_2$ below the top surface 250 of the outer tube 212, say at location x. At location x, the first negative electrode is electrically coupled to the first portion 252. In addition, the first negative electrode extends to the length $L_3$. A second tine, herein also referred to as a second of the plurality of negative electrodes 218 may also begin at length $L_2$ below the top surface 250 of the outer tube 212, and may further begin a location (x+$W_1$), where $W_1$ is a first spacing between the tines of the plurality of negative electrodes 218. At location (x+$W_1$), the second negative electrode of the second portion 256 is electrically coupled to the first portion 252. In addition, the second negative electrode of the second portion 256 extends to the length $L_3$, which is the same length to which the first negative electrode extends, for example. In a similar way, successive tines or negative electrodes of the plurality of negative electrodes 218 are formed on the inner surface 246 of the outer tube 212. The electrical wire 254 connects each of the first portion 252 and the second portion 256 to a negative terminal of the voltage supply located outside outer tube 212, thereby applying a negative voltage to each of the tines/electrodes of the plurality of negative electrodes 218. It may be noted that the outer tube 212 may not include any perforations, specifically in the regions where the plurality of negative electrodes 218 are formed. Thus, the plurality of negative electrodes 218 may be formed on a non-perforated cylindrical surface.

The central element 214 of the PM sensor 202 may include a plurality of electrodes 220 formed on an outer surface 268 of the central element 214. The plurality of electrodes 220 formed on the outer surface 268 of the central element 214 may be connected to a positive terminal of the voltage supply and hereafter be referred to as a plurality of positive electrodes 220. The plurality of positive electrodes 220 may be formed directly on the outer surface 268 of the central element 214, and hence may be in face-sharing contact with the outer surface 268 of the central element 214. The plurality of positive electrodes 220 may include a third unbranched portion 264, and a fourth branched portion (or tines) 266, both of which are formed along the outer surface 268 of the central element 214 and further housed within the outer tube 212. Though referred to as third portion 264 and fourth portion 266, it may be appreciated that the third portion 264 is a first unbranched portion of the plurality of positive electrodes 220 and the fourth portion 266 is a second branched portion of the plurality of positive electrodes 220. An electrical wire 258 may connect each of the third portion 264 and the fourth portion 266 to a positive terminal of the voltage supply located outside the outer tube 212. As such, a portion of the electrical wire 258 may be housed inside the outer tube 212 and the remainder may be housed outside the exhaust passage 204 (as one example, <1 meter away), and electrically coupled to the voltage supply and a measurement device which will be explained later with reference to FIG. 3A.

The fourth portion 266 of the plurality of positive electrodes 220 may beat a length $L_5$ (arrow 270) from the top surface 250 of the outer tube 212. In one example, the length $L_5$ at which the fourth portion 266 of the positive electrode 220 begins may be substantially equal to the length $L_2$ at which the second portion 256 of the plurality of negative electrodes 218 begin inside the outer tube 212. Thus, the plurality of positive electrodes 220 formed on the outer surface of the central element 214 may be at the same height as the plurality of negative electrodes 218 formed on the inner surface of the outer tube 212.

The fourth portion 266 may include a plurality of tines, each of the tines of length $L_6$ (arrow 272) formed at a second spacing ($W_2$) along the outer surface 268 of the central element 214. The second spacing $W_2$ may typically be in the range from 10 micrometers to 100 micrometers with a linewidth of each individual electrode being about the same value, although the latter is not necessary. In one example, the second spacing $W_2$ may be substantially equal to the first spacing $W_1$. In another example, the second spacing $W_2$ may be different from the first spacing $W_1$. In some examples, the second spacing $W_2$ may be adjusted based on the curvature of the central element 214 and the first spacing W1 such that the plurality of positive electrodes 220 face the plurality of negative electrodes 218. Thus, a tine or positive electrode of the plurality of positive electrodes 220 distributed along the inner surface 246 of the outer tube 212 may face a tine or negative electrode of the plurality of negative electrodes 218 distributed along the outer surface 268 of the central element 214.

The fourth portion 266 of the plurality of positive electrodes 220 may be evenly spaced and substantially parallel to the second portion 256 of the plurality of negative electrodes 218, and parallel to the central axis of the tubes Y-Y'. Said another way, the second portion 266 of the plurality of positive electrodes 220 may be perpendicular to the direction of exhaust flow (arrow 206) in the exhaust passage 204.

The third portion 264 of the plurality of positive electrodes 220 may be formed along an outer circumference of the central element 214 in a direction parallel to the direction of flow of exhaust (arrow 206) in the exhaust passage 204. The third portion 264 may be parallel to the first portion 252 of the plurality of negative electrodes 218.

As such, the third portion 264 may be formed at the length $L_5$ (arrow 270) from the top surface 250 of the outer tube 212. The third portion 264 may include a curvature and as such, the curvature may be substantially equal to the curvature of the central element 214. In effect, a length of the third portion 264 may be substantially equal to the outer circumference of the central element 214. Further, the fourth portion 266 may be electrically coupled to the third portion 264. For example, a first tine or first of the plurality of positive electrodes may begin at length $L_5$ below the top surface 250 of the outer tube 212, say at location y. The first positive electrode at location y may face the first negative electrode at location x, for example. At location y, the first positive electrode of the plurality of positive electrode 220 is electrically coupled to the third portion 264. In one example, the location y may be selected based on the location x of the first negative electrode and the gap ($D_2$–$D_1$). Thus, the first positive electrode may be across from the first negative electrode, for example. In addition, the first positive electrode of the fourth portion 266 of the plurality of positive electrode 220 extends to the length $L_6$ (arrow 272). In one example, the length $L_6$ may be substantially equal to the length $L_3$ of the second portion 256 of the plurality of negative electrodes 218. In another example, the length $L_6$ may be different from the length $L_3$ of the plurality of negative electrodes 218.

A second tine or second of the plurality of positive electrodes 220 may begin at length $L_5$ below the top surface 250 of the outer tube 212, and may further begin a location (y+$W_2$), where $W_2$ is a second spacing between the plurality of positive electrodes 220. At location (y+$W_2$), the second positive electrode of the plurality of positive electrodes 220 is electrically coupled to the third portion 264. In addition, the second positive electrode of the plurality of positive electrodes 220 extends to the length $L_6$, which is the same length to which the first positive electrode extends, for example. In a similar way, successive positive electrodes of the plurality of positive electrodes 220 are formed on the outer surface 268 of the central element 214. The electrical wire 258 connects each of the third portion 264 and the fourth portion 266 to a positive terminal of the voltage supply located outside outer tube 212, thereby applying a positive voltage to each of the electrodes of the plurality of positive electrodes 2620. It may be noted that the plurality of positive electrodes 220 is not electrically coupled to the plurality of negative electrodes 218. Thus, the third portion 264 is electrically isolated from each of the first portion 252 and the second portion 256. Likewise, the fourth portion 266 is electrically isolated from each of the first portion 252 and the second portion 256. Thus, the positive electrode 220 is not coupled to the negative electrode 218. The positive electrode 220 is not formed on the same surface as the negative electrode 218. As such, the gap separates the plurality of positive electrodes 220 from the plurality of negative electrodes 218. As such, there are no components in the gap. When the positive and negative voltages are applied to the respective electrodes, a uniform electric field is generated in the gap between the plurality of positive electrodes 220 and the plurality of negative electrodes 218. Specifically, the uniform electric field extends along the entire length of the plurality of positive and negative electrodes, and is further in a direction perpendicular to the surface of the plurality of electrodes. Thus, the electric field is normal to the outer surface 268 of the central element 214, and is further normal to the inner surface 246 of the outer tube 212. The electric field occurring normal to the surfaces may generate a stronger force on the charged particulates in the exhaust, thereby pushing the particulates towards the electrodes and accumulating the particulates on the electrodes. Moreover, the electrostatic field in the gap does not decay within the gap, and is more uniform across the gap.

As described earlier, the central element 214 includes the plurality of perforations 224 formed on the surface of the central element 214. As such, the plurality of perforations 224 may be interspersed between the plurality of positive electrodes 220 along a length of the central element. For example, between the first positive electrode and the second negative electrodes, a column of perforations may be formed. In one example, four equally spaced perforations may be formed between the first positive electrode and the second positive electrode of the plurality of positive electrodes 220. In other examples, a different number of perforations and/or perforations of different spacing between them may be provided.

The central element 214 includes a heating element 222 (herein also referred to as regeneration circuit) formed on an inner surface 248 of the central element 214. As such, the heating element 222 may be formed on a surface different from the surface on which the positive electrode 220 is formed. That is, while the positive electrodes are formed on an outer surface, the heating element is formed on the inner surface. In addition, the heating element 222 is separated from the positive electrode 220 by a distance equal to a thickness of the central element 214. The heating element 222 may comprise, but is not limited to, a temperature sensor, and a heater. Possible materials for the heater and the temperature sensor forming the heating element 222 may include platinum, gold, palladium, and the like; and alloys, oxides, and combinations comprising at least one of the foregoing materials, with platinum/alumina, platinum/palladium, platinum, and palladium. The heating element 222 may be used for regenerating the PM sensor 202. Specifically, during conditions when the particulate matter load or soot load of the PM sensor 202 is higher than a threshold, heating element 222 may be operated to burn accumulated soot particles from the surface of sensor. Operating the heating element includes closing a switch of a regeneration circuit coupled to the heating element to apply a current through the heating element for a threshold time, thereby raising a temperature of the heating element and subsequently of the sensor electrodes to burn off soot particulates deposited on the sensor electrodes.

Turning now to FIG. 3A, cross-sectional view 300 of the PM sensor 202 in a plane along line A-A' of FIG. 2 is shown. Herein, a cross-section of the outer tube 212 and the central element 214 is shown. As described earlier, the central element 214 may be a perforated hollow cylindrical tube with a diameter $D_2$ and the outer tube 212 may be a hollow cylindrical tube with a diameter $D_1$ (wherein $D_2<D_1$, for example). The central element 214 is positioned within the outer tube 212 such that both of the central element and the outer tube share a common central axis such that the circular cross-section of each of the central element and the outer tube have a common center.

As described earlier, the plurality of negative electrodes 218 are formed along the inner surface 246 of the outer tube 212. Successive electrodes of the plurality of negative electrodes are separated by the first spacing $W_1$. The plurality of negative electrodes 218 are connected to a negative terminal of a voltage supply 308 of an electric circuit 304. Briefly, the plurality of negative electrodes 218 are connected via the electric wire 254 to the negative terminal of the voltage supply 308 via a measuring device 318. The measuring device 318 may be an ammeter, voltmeter, and the like.

The plurality of positive electrodes 220 are formed along the outer surface 268 of the central element 214. Successive tines/electrodes of the plurality of positive electrodes are separated by the second spacing $W_2$. The plurality of positive electrodes 220 are connected to a positive terminal of the voltage supply 308 of the electric circuit 304 via the electric wire 258.

As described earlier, a portion of the exhaust gas enters the PM sensor 202 via the inlet in the inner tube of the PM sensor 202. The portion of the exhaust inside the inner tube then flows along the inner tube into the central element 214 (within region 320). The portion of the exhaust gas flowing in the region 320 within the central element 214 is flowing in a direction orthogonal to the exhaust flow inside the exhaust passage. The portion of the exhaust in the region 320 then flows through the plurality of perforations 224 as indicated by arrows 306. Thus, through the plurality of perforations 224 along the central element 214, the exhaust gas is directed in the gap 302 between the electrodes. When an electric field is applied between the electrodes, the particulates in the exhaust may get trapped on the surface of the electrodes and in the gap 302 between the electrodes, for example. As such, a particulate load or soot load on the PM sensor 202 may be determined based on changes in resistance (or current) between the electrodes as described below.

The voltage supply 308 and the measurement device 318 of the electric circuit 304 may be controlled by a controller, such as controller 12 of FIG. 1, so that particulate matter collected at the PM sensor may be used for diagnosing leaks in the DPF, for example. The electric wires 254 and 258, the voltage supply 308 and the measurement device 318 are part of the electric circuit 304 and are housed outside the exhaust passage 204 of FIG. 2. The measurement device 318 may be any device capable of reading a resistance (or current) across the electrodes, such as a voltmeter (ammeter). As PM or soot particles get deposited in the gap 302 between the positive and the negative electrodes, the current measured by the measuring device 318 may begin to increase. The controller 12 may be able to determine the current and infer a corresponding PM or soot load on the PM sensor 202. By monitoring the load on the PM sensor 202, the exhaust soot load downstream of the DPF may be determined, and thereby used to diagnose and monitor the health and functioning of the DPF.

As described earlier, the central element 214 includes the heating element 222 formed along the inner surface 248 of the central element 214. The heating element 222 may be used for regenerating the PM sensor 202. Specifically, during conditions when the particulate matter load or soot load of the PM sensor 202 is higher than a threshold, heating element 222 may be operated to burn accumulated soot particles from the surface of sensor. During PM sensor regeneration, the controller 12 may provide a voltage via a voltage supply 310, to the heating element 222. In addition, the controller may close the switch 312 for a threshold time to apply the voltage via the voltage supply 310 to the heating element 222 in order to raise the temperature of the heating element 222. Subsequently, when the electrodes and the gap 302 between the electrodes are sufficiently clean, the controller may open the switch 312 to stop heating the heating element 222. By intermittently regenerating the PM sensor 202, it may be returned to a condition (e.g., unloaded or partially loaded condition) more suitable for collecting exhaust soot. In this way, accurate information pertaining to the exhaust soot level may be inferred from the sensor regeneration and this information may be used by the controller for diagnosing leaks in the particulate filter.

Exhaust gas exiting the central element 214 via the plurality of perforations 224 may then flow into the outer tube 212, and thereafter be expelled into the exhaust passage as described with reference to FIG. 3B. The outlet holes 228 may be positioned such that exhaust gas may exit the PM sensor 202 is a direction orthogonal to the direction of exhaust flow (indicated by arrow 206) in the exhaust passage 204. Cross-sectional views taken along lines B-B' shown in FIG. 3B depict the position of the outlet holes in the outer tube 212 with respect to an exhaust flow direction.

Turning now to FIG. 3B, cross-sectional view 350 of the PM sensor 202 in a plane along line B-B' of FIG. 2 is shown. Herein, a cross-section of the outer tube 212 and the inner tube 216 is shown. As described earlier, the inner tube 216 may be a hollow cylindrical tube with a diameter $D_3$ and the outer tube 212 may be a hollow cylindrical tube with a diameter $D_1$. The inner tube 216 is positioned within the outer tube 212 such that both of the inner and the outer tubes share a common central axis.

Exhaust gas flow through the exhaust passage is along the X-axis, as indicated by the arrow 206. A portion of the exhaust enters the PM sensor 202 via the inlet 226 of the inner tube. The portion of the exhaust then flows along the Y-axis inside the inner tube (within region 356) and towards the central element 214. In the cross-sectional view 350 taken along line B-B', exhaust gas is confined to the inner tube 216, and further flows perpendicular to and out of the plane of the paper (along Y-axis). Exhaust gas may exit the central element via perforations interspersed between the positive electrodes. As such, the exhaust gas may first travel through the gap formed between the central element and the outer tube (gap between the electrodes, for example), and then travels in the annular space/region 354 formed between the outer tube and the inner tube. In view 350, exhaust gas is confined in the annular space 354 and is flowing into the plane of the paper (along Y-axis). Thus, exhaust flows in the annular space 354 in a direction opposite to exhaust flow in the region 356 of the inner tube 216.

The outer tube 212 may include outlet holes 228 positioned on diametrically opposite surfaces of the outer tube 212. Specifically, the portion of the exhaust gas flowing within the annular space 354 between the outer and inner tube may exit via the outlet holes 228. In one example, the outlet holes 228 may be holes cut out on diametrically opposite surfaces of the outer tube 212. Various other geometries of the outlet holes 228 may be possible without deviating from the scope of the disclosure. Other example geometries include, slits, apertures and the like.

The outlet holes 228 are positioned such that the portion of the exhaust gas flowing in the annular space 354 exits the PM sensor along the Z-axis (as indicated by arrow 352). As such, the portion of the exhaust gas flowing out may exit the outer tube 212 in a direction orthogonal to the exhaust flow direction (arrow 206).

Thus, an example particulate matter sensor may include an outer, non-perforated tube with a plurality of negative electrodes along an inner surface, a central, perforated element with a plurality of positive electrodes along an outer surface of the central element, the central element positioned within the outer tube, and an inner tube appended to the central element, each of the outer tube, the central element, and the inner tube having a common axis. Additionally or alternatively, the central element may include a regeneration circuit coupled to an inner surface of the central element for heating the central element, and wherein the central element comprises a plurality of perforations, the plurality of perforations extending through each of the outer surface and the inner surface of the central element. Additionally or alternatively, a diameter of the inner tube may be smaller than each of a diameter of the outer tube, and a diameter of the central element. Additionally or alternatively, the plurality of positive electrodes may face the plurality of negative electrodes and are separated from the plurality of negative electrodes by a gap. Additionally or alternatively, the plurality of negative electrodes may be distributed along the inner surface of the outer tube at a first spacing, and wherein the plurality of positive electrodes may be distributed along the outer surface of the central element at a second spacing, the plurality of perforations of the central element interspersed between the plurality of positive electrodes. Additionally or alternatively, the first spacing may be substantially equal to the second spacing. Additionally or alternatively, the first spacing may be different from the second spacing. Additionally or alternatively, the inner tube may comprise a first region and a second region, and wherein first region is positioned within the outer tube, and the second region extends out of the outer tube into an exhaust pipe, the central element being appended to the inner tube at the first region of the inner tube. Additionally or alternatively the second region may comprise an inlet configured to allow exhaust gas in the exhaust pipe to enter the PM sensor assembly via the inlet in a direction opposite to a direction of exhaust flow in the exhaust pipe and flow from the second region towards each of the first region, the central element, and the gap, the exhaust gas flowing from the central element to the gap through the plurality of perforations. Additionally or alternatively, the outer tube may include outlet holes configured to direct the exhaust gas from the assembly to the exhaust pipe in a direction orthogonal to each of the direction of exhaust flow in the exhaust pipe, and to a direction of entry of the exhaust gas into the assembly via the inlet.

As such, the sensitivity of the PM sensor may be affected by large particulates and/or water droplets getting deposited on the positive and negative electrodes. It may be possible to filter out larger particulates and water droplets at the inlet of the inner tube as shown in FIG. 4.

Turning now to FIG. 4, schematic view 400 shows exhaust flow through the PM sensor 202. Specifically, view 400 depicts exhaust flowing into the PM sensor 202 via the inlet 226 of the inner tube 216 and thereon into the guiding tube 210. View 400 further depicts exhaust flowing out of the PM sensor 202 via the outlet holes 228 of the outer tube 212.

Similar to FIG. 2, FIG. 4 shows example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with a space there-between and no other components may be referred to as such, in at least one example.

Exhaust gas flows along the X-axis inside the exhaust passage 204 as indicated by the arrow 206 from an upstream particulate filter towards PM sensor 202, for example. Exhaust gas may include contaminants 402 such as larger particulates and water droplets. The inlet 226 is positioned in the inner tube 216 such that exhaust enters the inlet in a direction indicated by arrow 208, opposite to the flow of exhaust (206) in the exhaust passage 204. The inlet 226 is positioned closer to an end of the exhaust tailpipe and further away from the particulate filter upstream of the PM sensor 202. As exhaust flows in the exhaust passage 204, in a region around the inlet 226, a static pressure gradient is created. Herein, a higher static pressure exists at and near the inlet 226 than at regions away from the inlet 226, and as a result, exhaust gas gets steered into the PM sensor 202 via the inlet 226. The portion of the exhaust gas entering via the inlet 226 undergoes a reversal in flow direction prior to entering the sensor. The contaminants 402 may be large in size and thus may not be affected by the static pressure gradient generated at and near the inlet 226. The contaminants 402 may continue to flow past the PM sensor 202 in the exhaust passage, and be expelled out of the exhaust pipe. Therefore, the sensor electrodes of the PM sensor positioned within the outer tube 212 may be protected from impingement of water droplets and larger particulates. In this way, by creating a static pressure gradient at the inlet and steering the exhaust in a reverse direction into the PM sensor via the inlet, it may be possible to filter out larger particulates and water droplets thereby reducing the amount of contaminants entering the PM sensor 202. In this way, the PM sensor may be protected from impingement of water droplets and larger particulates and the PM sensor may be made more reliable. Overall, the functioning of the PM sensor to estimate the filtering capabilities of the DPF (and thereby to detect DPF leaks) may be increased and exhaust emissions compliance may be boosted as particulates in the exhaust may be detected more accurately and reliably.

As described earlier, the portion of the exhaust entering the PM sensor 202 via the inlet 226 may flow in the region within the inner tube as indicated by arrow 404 (along Y-axis) and into the central element 214. Exhaust may then flow from the inside of the central element 214 through the plurality of perforations 224 into the gap between the electrodes (as indicated by arrow 406). As such, the exhaust may flow radially through the plurality of perforations 224 into the gap wherein the particulates in the exhaust may experience the uniform electric fields and get deposited in the gap and on the electrode surfaces. Exhaust then flows into the outer tube 212 (as indicated by arrow 408). The outer tube 212 includes outlet holes 228 positioned on diametrically opposite surfaces of the outer tube 212. Exhaust then flows out of the PM sensor 202 via the outlet holes 228 as indicated by arrow 410. Herein, the exhaust exits the PM sensor 202 in a direction orthogonal to the direction of exhaust flow entering the PM sensor 202 via the inlet 226. In addition, the exhaust exits the PM sensor 202 in a direction orthogonal to the exhaust flow in the exhaust passage (indicated by arrow 206).

Thus, an example particulate matter sensor includes evenly spaced negative electrodes formed on a first cylindrical element, evenly spaced positive electrodes formed on a second cylindrical element, the positive electrodes separated from negative electrodes by a gap and positioned facing the negative electrodes, and heating elements formed on the second element, the positive electrodes and the heating elements formed on different surfaces of the second element. Additionally or alternatively, the second element may be positioned coaxially within the first element. Additionally or alternatively, the second element may comprise a perforated region, the perforated region comprising the positive electrodes, the heating elements, and a plurality of perforations, and wherein the positive electrodes are formed on an outer surface of the perforated region, the heating elements formed on an inner surface of the perforated region, and the plurality of perforations dispersed between the positive electrodes and the heating elements. Additionally or alternatively, the second element may further comprise a non-perforated region, the non-perforated region different from the perforated region and wherein the non-perforated region is coaxial to the perforated region and is smaller in diameter than the perforated region. Additionally or alternatively, the non-perforated region may comprise an inlet configured to allow an exhaust gas to enter the sensor and flow from the non-perforated region towards the perforated region and out into the gap via the plurality of perforations. Additionally or alternatively, the first element may comprise outlet holes configured to allow the exhaust gas to exit the sensor.

Figure 5:
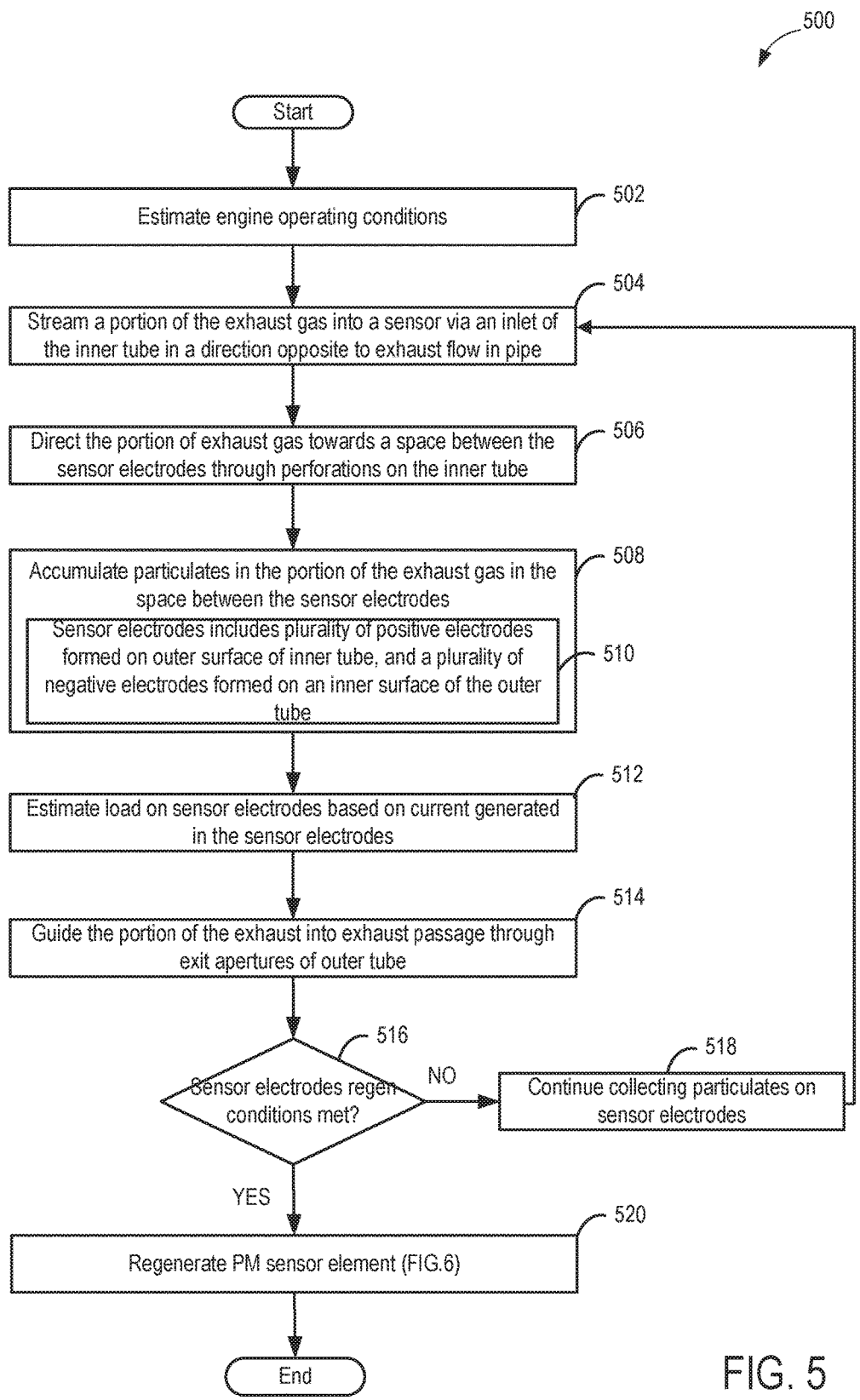
FIG. 5 shows a flow chart depicting a method for accumulating particulates in the exhaust flow across sensor electrodes separated by a gap positioned within the PM sensor.

Turning now to FIG. 5, a method 500 for accumulating particulates in the exhaust flow across sensor electrodes positioned within the PM sensor (such as a PM sensor 106 shown at FIG. 1, and/or PM sensor 202 of FIG. 2, for example) is shown. Specifically, the particulates in the exhaust flow may be trapped in a gap formed between the positive and negative electrodes of the PM sensor. Herein, the positive electrodes are formed on an outer surface of a perforated central element, and the negative electrodes are formed on an inner surface of a non-perforated outer tube. The central element may be a cylindrical perforated hollow tube positioned coaxially within the cylindrical outer tube.

Instructions for carrying out method 500 and the rest of the methods 600 and 700 included herein may be executed by a controller based on instructions stored on a memory of the controller and in conjunction with signals received from sensors of the engine system, such as the sensors described above with reference to FIGS. 1-4. The controller may employ engine actuators of the engine system to adjust engine operation, according to the methods described below.

At 502, method 500 includes determining and/or estimating engine operating conditions. Engine operating conditions determined may include, for example, engine speed, exhaust flow rate, engine temperature, exhaust air-fuel ratio, exhaust temperature, duration (or distance) elapsed since a last regeneration of the DPF, PM load on PM sensor, boost level, ambient conditions such as barometric pressure and ambient temperature, etc.

Method 500 proceeds to 504 where a portion of the exhaust gas is streamed into the PM sensor via an inlet. Streaming the exhaust gas into the PM sensor inlet includes reversing a direction of exhaust flowing through the exhaust passage prior to flowing the exhaust into the sensor inlet. As such, the inlet may be formed on an inner tube, specifically on a portion of the inner tube that extends into the exhaust passage. The inner tube may include a larger perforated portion coupled to a smaller non-perforated portion. Herein, the inlet is formed on the smaller non-perforated portion. Further, the inlet may be formed on the inner tube such that exhaust gas enters the inlet in a direction opposite to the direction of exhaust flow inside the exhaust passage. A higher static pressure is created in and around the inlet in the inner tube. As a result, a larger portion of the exhaust flows into the PM sensor via the inlet. In addition, larger particulates and water droplets in the exhaust remain unaffected by the higher static pressure. Thus, the larger particulates and water droplets do not enter the PM sensor via the inlet, thereby reducing sensor errors due to these particulates depositing on the sensitive electrode surface, for example.

The method proceeds to 506. At 506, the portion of the exhaust entering via the inlet is directed towards a space or gap between sensor electrodes through perforations in the inner tube. As described earlier, the sensor electrodes include a plurality of negative electrodes formed on an inner surface of the outer tube of the PM sensor. The sensor electrodes further include a plurality of positive electrodes formed on an outer surface of the perforated portion of the inner tube. As such, the inner tube positioned within the outer tube is separated by a gap from the outer tube. Thus, the plurality of positive electrodes are separated from the plurality of negative electrodes by the gap. The portion of the exhaust gas inside the non-perforated portion of the inner tube travels into the perforated portion of the inner tube and is released via the plurality of perforations into the gap between the outer tube and the inner tube. The method then proceeds to 508.

At 508, particulates in the portion of the exhaust streaming through the perforations are retained/accumulated in the gap between the sensor electrodes. Herein, the sensor electrodes includes the plurality of positive electrodes distributed along the outer surface of the inner tube, and the plurality of negative electrodes distributed along an inner surface of an outer tube of the PM sensor. It may be appreciated that the plurality of positive electrodes are formed along the perforated portion of the inner tube. As such, the plurality of perforations may be interspersed between the plurality of the positive electrodes formed on the inner tube.

As explained earlier, the plurality of positive electrodes and the plurality of negative electrodes are positioned facing each other. The plurality of positive electrodes formed on the outer surface of the central element are connected to the positive terminal of a voltage supply. Similarly, the plurality of negative electrodes formed on the inner surface of the outer tube are connected to a measurement device and then to the negative terminal of the voltage supply. When the controller applies a voltage to the sensor electrodes, a uniform electric field is generated in the gap between the electrodes. Thus, particulates entering the gap via the plurality of perforations on the inner tube may experience a strong and uniform electric field in the gap, enabling them to be accumulated as a soot bridge in the gap between the electrodes. The method then proceeds to 512.

At 512, a load on the sensor electrodes is estimated based on a current generated in the sensor electrodes. When particulates accumulate on the surface of the sensor electrodes and soot bridges form in the gap between the sensor electrodes, the resistance of the electrodes starts decreasing and a current measured by the measurement device starts to increase. The controller may be able to deduce a load on the sensor electrodes based on the current measured across the electrodes.

Method 500 then proceeds to 514, where the portion of the exhaust exiting the sensor electrodes is guided into the outer tube and then into the exhaust passage through outlet holes or exit apertures positioned on side surfaces of the outer tube. As such, the outlet holes on the outer tube may guide the exhaust in a direction orthogonal to each of the flow of the exhaust gas in the exhaust pipe, and a direction of flow of the portion of the exhaust gas into the sensor via the inlet. Method 500 proceeds to 516.

At 516, method 500 includes determining if the sensor electrode regeneration conditions are met. Specifically, when the soot load on the PM sensor is greater than the threshold, or when a resistance of the PM sensor (adjusted for temperature) drops to a threshold resistance, or when a current of the PM sensor is greater than a threshold current, PM sensor regeneration conditions may be considered met. In some examples, if a threshold time has elapsed since an immediately previous sensor regeneration, regeneration condition may be considered met. The PM sensor may require regeneration to enable further PM detection.

Figure 6:
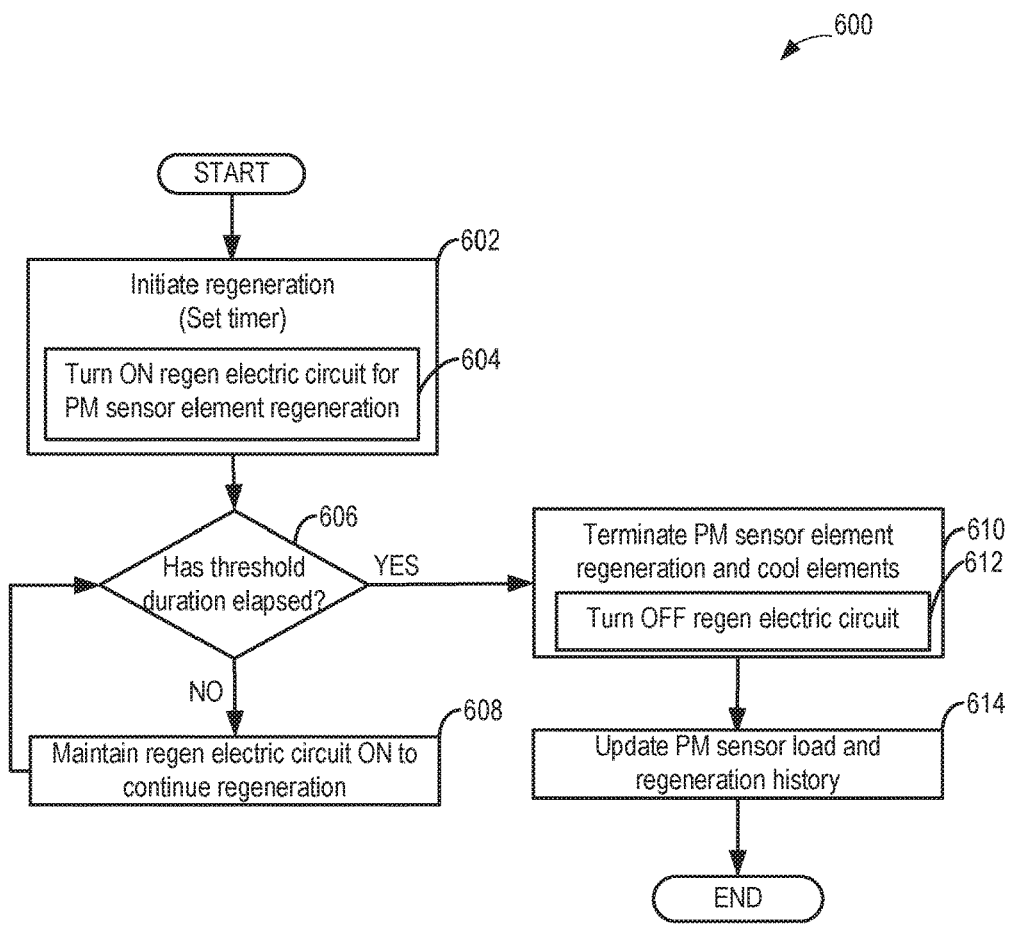
FIG. 6 is a flow chart depicting an example method for regenerating the sensor electrodes of the PM sensor.

If regeneration conditions are met (e.g., "YES" at 516), then method 500 proceeds to 520 where the PM sensor may be regenerated by performing a method described in FIG. 6. Briefly, regeneration of the PM sensor may be initiated by heating up the sensor. The PM sensor may be heated by actuating a heating element coupled thermally to the inner surface of the inner perforated tube (also known as central element), for example. Herein, the controller may close the switch in the electric circuit, thereby applying a voltage to the heating element, causing the heating elements to heat up. Further, the controller may not apply voltages to the sensor electrodes while regenerating the sensor. Thus, the sensor electrodes may not accumulate soot during the sensor regeneration. As such, the heating element may be actuated until the soot load of the sensor has been sufficiently reduced by oxidation of the carbon particles between the electrodes.

However, if PM sensor regeneration conditions are not met (e.g., "NO" at 516), then method proceeds to 518 where the particulates may continue to be collected on the sensor electrodes.

Thus an example method for particulate matter sensing is shown. The method includes streaming a portion of exhaust gas from downstream of a particulate filter into a sensor via an inlet of an inner tube in a direction opposite to flow of the exhaust gas in an exhaust pipe, directing the portion of the exhaust gas towards a space between sensor electrodes through a plurality of perforations of the inner tube, the plurality of perforations located distal to the inlet of the inner tube, accumulating particulates in the portion of the exhaust gas in the space between the sensor electrodes, and guiding the portion of the exhaust gas out of the sensor via outlet holes positioned on an outer tube in a direction orthogonal to each of the flow of the exhaust gas in the exhaust pipe, and a direction of flow of the portion of the exhaust gas into the sensor via the inlet. Additionally or alternatively, the sensor electrodes may comprise a plurality of positive electrodes formed on an outer surface of the inner tube and a plurality of negative electrodes formed on an inner surface of the outer tube, the inner tube positioned within the outer tube and further separated by the space. Additionally or alternatively, the method includes determining a load on the sensor electrodes based on a current generated in the sensor electrodes, and further comprising regenerating the sensor electrodes by heating electric elements formed on an inner surface of the inner tube when the load on the sensor electrodes is higher than a threshold load.

As such, the PM sensor may include a controller with computer readable instructions stored on non-transitory memory for accumulating particulates in the exhaust gas in the gap by applying a positive voltage to the positive electrodes and a negative voltage to the negative electrodes, determining a load on the sensor based on a current generated between the positive electrodes and the negative electrodes, and responsive to the load being higher than a first threshold, regenerate the sensor (as shown in FIG. 6) by applying a voltage to the heating elements until the soot load is lower than a second threshold, the second threshold being lower than the first threshold.

Turning now to FIG. 6, a method 600 for regenerating the PM sensor (such as a PM sensor 106 shown at FIG. 1, and/or PM sensor 202 of FIG. 2, for example) is shown. Specifically, when the soot load on the PM sensor is greater than the threshold, or when a resistance of the PM sensor adjusted for temperature drops to a threshold resistance, the PM sensor regeneration conditions may be considered met, and the PM sensor may require regeneration to enable further PM detection. At 602, regeneration of the PM sensor may be initiated and the PM sensor may be regenerated by heating up the sensor at 604. The PM sensor may be heated by actuating a heating element (such as heating element 222 formed on the inner surface 248 of the central element 214 of FIG. 2) until the soot load of the sensor has been sufficiently reduced by oxidation of the carbon particles between the electrodes. The PM sensor regeneration is typically controlled by using timers and the timer may be set for a threshold duration at 602. Alternatively, the sensor regeneration may be controlled using a temperature measurement of the sensor tip, or by the control of power to the heater, or any or all of these. When a timer is used for PM sensor regeneration, then method 600 includes checking if the threshold duration has elapsed at 606. If the threshold duration has not elapsed (e.g., "NO" at 606), then method 600 proceeds to 608 where the regeneration circuit may be kept ON to continue regeneration. If threshold duration has elapsed (e.g., "YES" at 606), then method 600 proceeds to 610 where the PM sensor regeneration may be terminated and the electric circuit may be turned off at 612. Further, the sensor electrodes may be cooled to the exhaust temperature for example. Method 600 proceeds to 614 where the PM sensor load and regeneration history may be updated and stored in memory. For example, a frequency of PM sensor regeneration and/or an average duration between sensor regenerations may be updated and the method ends.

The engine exhaust passage may include one or more PM sensors positioned upstream and/or downstream of the DPF for determining a soot load of the DPF. When the PM sensor is positioned upstream of the DPF, based on the resistance change following soot deposited on the plurality of electrodes of the PM sensor, a soot load on the sensor may be inferred. The soot load thus determined, may be used to update the soot load on the DPF, for example. If the soot load on the DPF is greater than a threshold for DPF regeneration, then the controller may adjust engine operating parameters to regenerate the DPF. Specifically, responsive to filter regeneration conditions being met, a temperature of the filter (or in the vicinity of the filter) may be sufficiently raised to burn off stored soot. This may include operating a heater coupled to the DPF, or raising a temperature of engine exhaust (e.g., by operating rich) flowed into the DPF.

Figure 7:
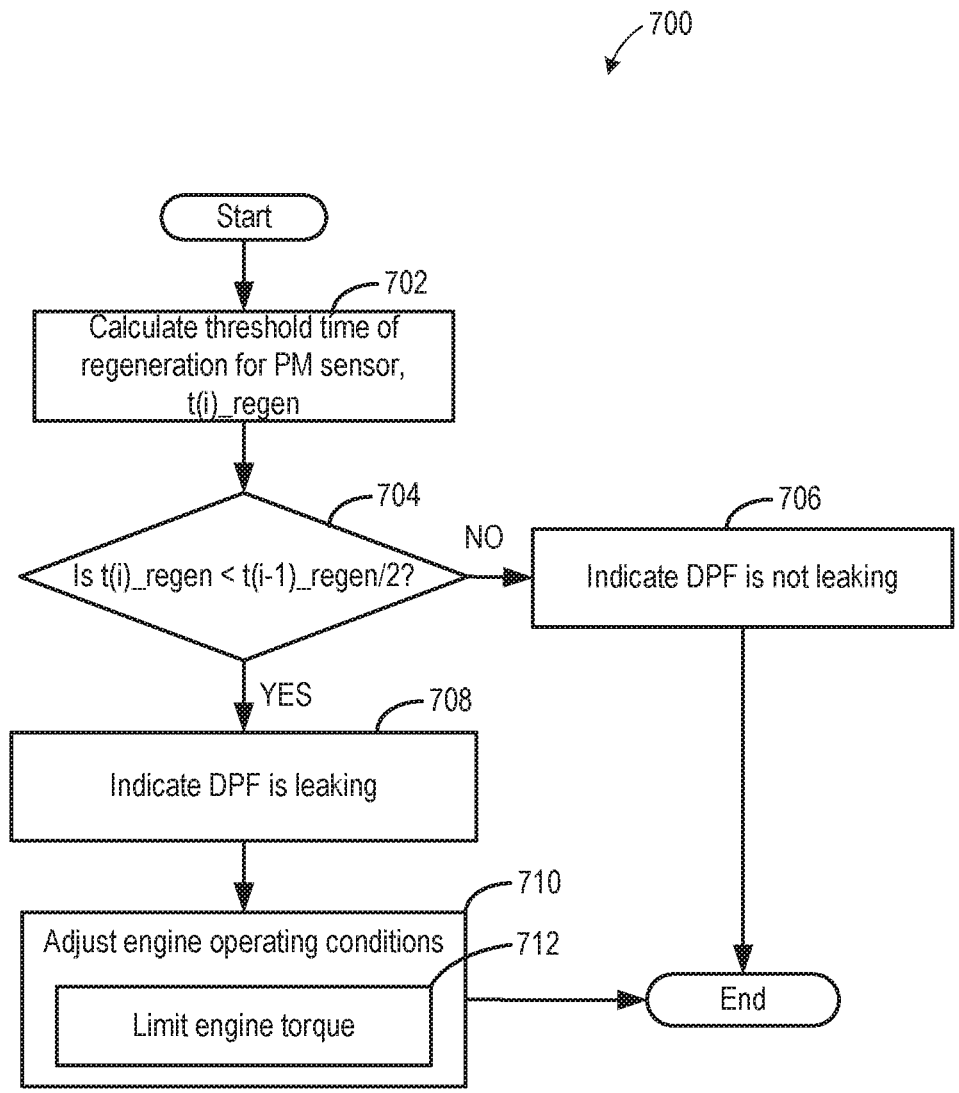
FIG. 7 shows a flow chart depicting an example method for diagnosing leaks in a particulate filter positioned upstream of the PM sensor.
Figure 8:
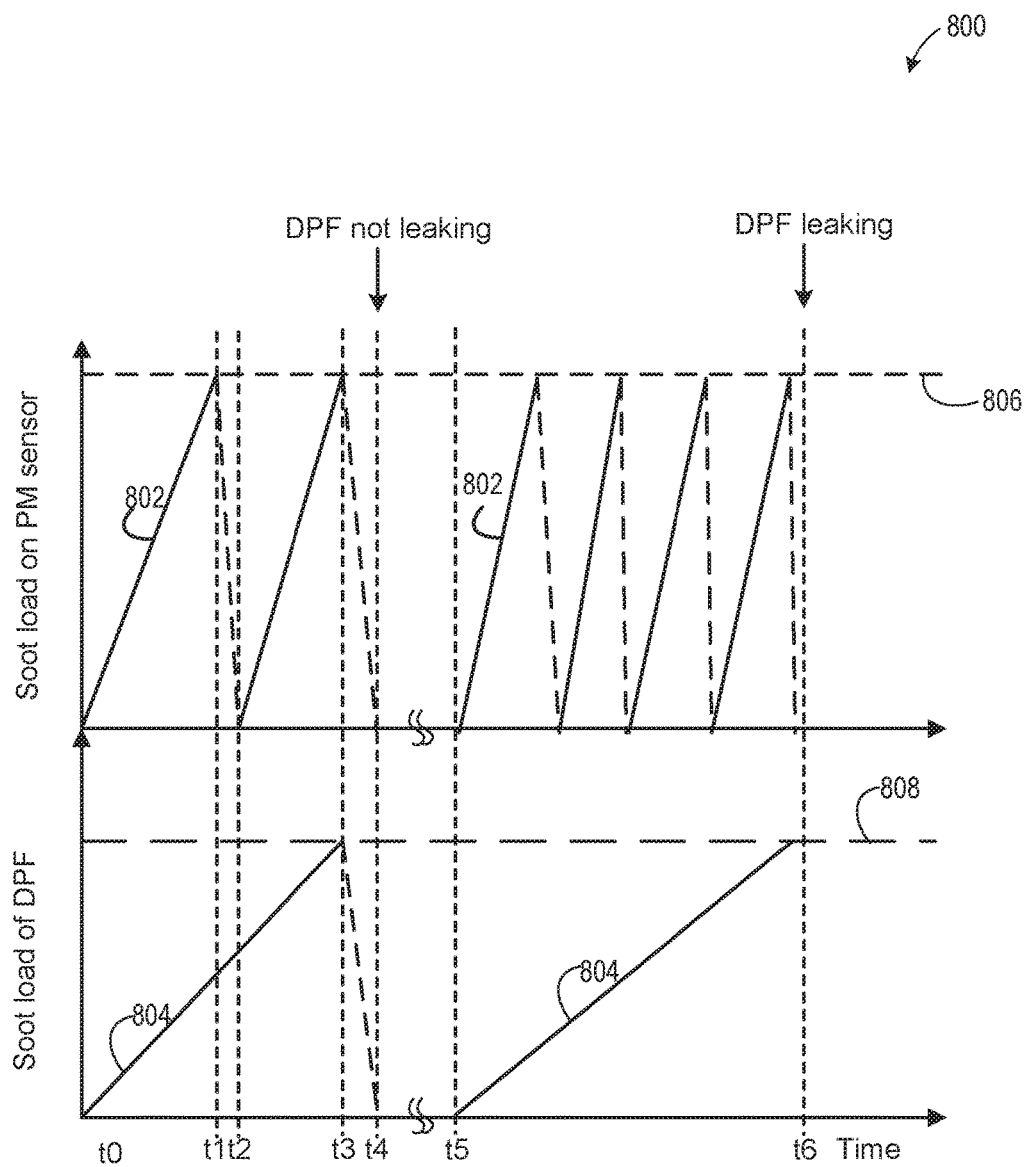
FIG. 8 shows an example relationship between a soot load on the PM sensor, and a soot load on a particulate filter positioned upstream of the PM sensor.

Turning now to FIG. 7, an example method 700 for diagnosing DPF function based on the regeneration time of the PM sensor is shown. At 702, it may be calculated by the controller, through calibration, the time of regeneration for the PM sensor, t(i)_regen, which is the time measured from end of previous regeneration to the start of current regeneration of the PM sensor. At 704, compare t(i)_regen to t(i−1)_regen, which is the previously calibrated time of regeneration of the PM sensor. From this, it may be inferred that the soot sensor may cycle through regeneration multiple times in order to diagnose the DPF. If the t(i)_regen is less than half the value of t(i−1) region, then at 708 indicate DPF is leaking, and DPF degradation signal is initiated. Alternatively, or additionally to the process mentioned above, the DPF may be diagnosed using other parameters, such as exhaust temperature, engine speed/load, etc. The degradation signal may be initiated by, for example, a malfunction indication light on diagnostic code. In addition, method 700 includes adjusting engine operation based on indicating leak in the DPF at 710. Adjusting engine operation may include limiting engine torque at 712, for example. In one examples, responsive to detecting leak in the DPF, engine power and torque may be reduced. Reducing the engine power and torque may reduce the amount of PM emissions in the exhaust. For example, adjusting engine operation may include reducing fuel injected in a diesel engine under heavy load conditions thereby reducing torque. Additionally or alternatively, responsive to detecting leak in the DPF, an EGR usage may be decreased. Additionally or alternatively, an engine warning sign may appear on the dashboard to indicate a distance that the vehicle may be able to travel before a DPF service check.

A current regeneration time of less than half of the previous regeneration time may indicate that the time for electric circuit to reach the R_regen threshold is significantly shorter, and thus the frequency of regeneration is higher. Higher frequency of regeneration in the PM sensor may indicate that the outflowing exhaust gas is composed of a higher amount of particulate matter than realized with a normally functionally DPF. Thus, if the change of regeneration time in the soot sensor reaches threshold, t_regen, in which the current regeneration time of the PM sensor is less than half of that of the previous regeneration time, a DPF degradation, or leaking, is indicated, for example via a display to an operator, and/or via setting a flag stored in non-transitory memory coupled to the processor, which may be sent to a diagnostic tool coupled to the processor. If the change in regeneration time of the soot sensor does not reach threshold t_regen, then at 706 DPF leaking is not indicated. In this way, leaks in a particulate filter positioned upstream of the particulate matter sensor may be detected based on a rate of deposition of the particulates on the particulate matter sensor electrodes.

Turning now to FIG. 8, map 800 shows an example relationship between soot load on the PM sensor and the soot load on the particulate filter. Specifically, map 800 shows a graphical depiction of the relationship between PM sensor regeneration and the soot load of the DPF, specifically how PM sensor regeneration may indicate DPF degradation. Vertical markers t0, t1, t2, t3, t4, t5 and t6 identify significant times in the operation and system of PM sensor and DPF.

The first plot of FIG. 8 shows a soot load on the PM sensor. As previously described, PM gets deposited across the gap between the plurality of positive and negative electrodes. Herein, the electrodes are formed different cylindrical surfaces. Thus, soot gets accumulated in the gap between the electrodes forming soot bridges. As soot gets accumulated, a current measured across the electrodes beings to increase (or a resistance of the electrodes begins to decrease). The controller may be able to determine a soot load (plot 802) based on the current/resistance measured. As such, the soot load is at its lowest value at the bottom of the plots and increases in magnitude toward the top of the plot in the vertical direction. The horizontal direction represents time and time increases from the left to the right side of the plot. Horizontal marker 806 represents the threshold load for regeneration of the PM sensor in the top plot. Plot 804 represents the soot load on the DPF, and the horizontal marker 808 represents the threshold soot load of DPF in the second plot.

Between t0 and t1, a PM sensor regeneration cycle is shown. At time t0, the PM sensor is in a relatively clean condition, as measured by low PM load (plot 802). A controller coupled to the PM sensor determines the soot load of the PM sensor based on the current/resistance measured across the sensor electrodes, for example. When the controller determines the soot load to be small, it may send instructions to a regeneration circuit to end supplying heat, so that a detection circuit may begin detecting PM load accumulation. As PM load increases on the sensor, soot gets accumulated in the gap between the sensor electrodes.

Between t0 and t1, PM continues to accumulate the soot load (plot 802) increases accordingly and further soot load on DPF also increases (plot 804). In some examples, soot load on the DPF may be based on PM sensor load when PM sensor is located upstream of DPF, for example.

At t1, the soot load on the PM sensor (plot 802) reaches the threshold load for regeneration of the PM sensor (marker 806). The threshold load may a load at which the sensor may require regeneration. At t1, PM sensor regeneration may be initiated as explained earlier. Briefly, the controller may close a switch in the electric circuit to apply voltage to the heating elements formed along the inner surface of the central element, for example. In addition, the PM sensor may not be operated in PM accumulation mode, thus the controller may not apply any voltage to the sensor electrodes.

Thus, between t1 and t2, the PM sensor may be regenerated by turning on the electric circuit for regeneration. At t2, the PM sensor may be sufficiently cool, and may begin to accumulate soot and continue accumulating between t2 and t3 (DPF regeneration cycle), for example. During time between t2 and t3, DPF soot load continues to increase (plot 804). However, at t3, the soot load on the DPF (plot 804) reaches the threshold soot load for DPF regeneration (marker 808). Between t3 and t4, the DPF may be regenerated to burn off the soot deposited on the DPF. Further at t4, the PM sensor regeneration frequency may be compared with a previously estimated regeneration frequency of the PM sensor. Based on the PM sensor regeneration frequency remaining similar to previous cycles, the DPF may be determined to be not leaking. In this way, based on PM sensor output, DPF health may be monitored and diagnosed for leaks.

Between t5 and t6, another DPF cycle is shown. Herein, between t5 and t6, the soot load on the DPF gradually increases (plot 804). During this time, the soot load on the PM sensor (plot 802) may be monitored. Plot 802 shows the PM sensor going through multiple regeneration cycles as described earlier. However, the frequency of regeneration of the PM sensor has nearly doubled (plot 802). The higher frequency of regeneration in the PM sensor may indicate that the outflowing exhaust gas is composed of a higher amount of particulate matter than realized with a normally functional DPF. Therefore at t6, DPF leakage may be indicated.

In this way, a more accurate measure of the exhaust PM load, and thereby the DPF soot load can be determined. As such, this increases the efficiency of filter regeneration operations. In addition, by enabling more accurate diagnosis of an exhaust DPF, exhaust emissions compliance may be increased. As such, this reduces the high warranty costs of replacing functional particulate filters and exhaust component life is extended.

In this way, by separating the positive and negative electrodes of a PM sensor by a gap and forming the electrodes on distinct cylindrical surfaces of the PM sensor, electrostatic fields may be generated across the gap and normal to each of the cylindrical surfaces. The technical effect of separating the electrodes and generating electrostatic fields that are normal in the gap between the electrodes is that the electrostatic fields generated in the gap may be more uniform, boosting soot capture. By improving soot accumulation, PM sensor sensitivity is increased, thereby measuring PMs exiting the DPF more accurately and reliably. As a result, any leaks or degradation of the DPF may be detected more efficiently and effectively and exhaust emissions are improved.

The systems and methods described above provide for a particulate matter sensor comprising an outer, non-perforated tube with a plurality of negative electrodes along an inner surface, a central, perforated element with a plurality of positive electrodes along an outer surface of the central element, the central element positioned within the outer tube, and an inner tube appended to the central element, each of the outer tube, the central element, and the inner tube having a common axis. In a first example of the particulate matter sensor, the sensor may additionally or alternatively include wherein the central element comprises a regeneration circuit coupled to an inner surface of the central element for heating the central element, and wherein the central element comprises a plurality of perforations, the plurality of perforations extending through each of the outer surface and the inner surface of the central element. A second example of the particulate matter sensor optionally includes the first example and further includes wherein a diameter of the inner tube is smaller than each of a diameter of the outer tube, and a diameter of the central element. A third example of the particulate matter sensor optionally includes one or more of the first and the second examples, and further includes wherein the plurality of positive electrodes face the plurality of negative electrodes and are separated from the plurality of negative electrodes by a gap. A fourth example of the particulate matter sensor optionally includes one or more of the first through the third examples, and further includes wherein the plurality of negative electrodes are distributed along the inner surface of the outer tube at a first spacing, and wherein the plurality of positive electrodes are distributed along the outer surface of the central element at a second spacing, the plurality of perforations of the central element interspersed between the plurality of positive electrodes. A fifth example of the particulate matter sensor optionally includes one or more of the first through the fourth examples, and further includes wherein the first spacing is substantially equal to the second spacing. A sixth example of the particulate matter sensor optionally includes one or more of the first through the fifth examples, and further includes wherein the first spacing is different from the second spacing. A seventh example of the particulate matter sensor optionally includes one or more of the first through the fifth examples, and further includes wherein the inner tube comprises a first region and a second region, and wherein first region is positioned within the outer tube, and the second region extends out of the outer tube into an exhaust pipe, the central element being appended to the inner tube at the first region of the inner tube. An eighth example of the particulate matter sensor optionally includes one or more of the first through the seventh examples, and further includes wherein the second region comprises an inlet configured to allow exhaust gas in the exhaust pipe to enter the particulate matter sensor via the inlet in a direction opposite to a direction of exhaust flow in the exhaust pipe and flow from the second region towards each of the first region, the central element, and the gap, the exhaust gas flowing from the central element to the gap through the plurality of perforations. A ninth example of the particulate matter sensor optionally includes one or more of the first through the eighth examples, and further includes wherein the outer tube includes outlet holes configured to direct the exhaust gas from the particulate matter sensor into the exhaust pipe in a direction orthogonal to each of the direction of exhaust flow in the exhaust pipe, and to a direction of entry of the exhaust gas into the particulate matter sensor via the inlet.

The systems and methods described above also provide for a method of particulate matter sensing, in a particulate matter sensor system, the method comprising streaming a portion of exhaust gas from downstream of a particulate filter into a sensor via an inlet of an inner tube in a direction opposite to flow of the exhaust gas in an exhaust pipe, directing the portion of the exhaust gas towards a space between sensor electrodes through a plurality of perforations of the inner tube, the plurality of perforations located distal to the inlet of the inner tube, accumulating particulates in the portion of the exhaust gas in the space between the sensor electrodes, guiding the portion of the exhaust gas out of the sensor via outlet holes positioned on an outer tube in a direction orthogonal to each of the flow of the exhaust gas in the exhaust pipe, and a direction of flow of the portion of the exhaust gas into the sensor via the inlet. In a first example of the method, the method may additionally or alternatively include wherein the sensor electrodes comprises a plurality of positive electrodes formed on an outer surface of the inner tube and a plurality of negative electrodes formed on an inner surface of the outer tube, the inner tube positioned within the outer tube and further separated by the space. A second example of the method optionally includes the first example, and further comprising determining a load on the sensor electrodes based on a current generated in the sensor electrodes, and further comprising regenerating the sensor electrodes by heating electric elements formed on an inner surface of the inner tube when the load on the sensor electrodes is higher than a threshold load.

The systems and methods described above provide for a particulate matter sensor comprising evenly spaced negative electrodes formed on a first cylindrical element, evenly spaced positive electrodes formed on a second cylindrical element, the positive electrodes separated from negative electrodes by a gap and positioned facing the negative electrodes, and heating elements formed on the second element, the positive electrodes and the heating elements formed on different surfaces of the second element. In a first example of the particulate matter sensor, the sensor may additionally or alternatively include wherein the second element is positioned coaxially within the first element. A second example of the particulate matter sensor optionally includes the first example and further includes wherein the second element comprises a perforated region, the perforated region comprising the positive electrodes, the heating elements, and a plurality of perforations, and wherein the positive electrodes are formed on an outer surface of the perforated region, the heating elements formed on an inner surface of the perforated region, and the plurality of perforations dispersed between the positive electrodes and the heating elements. A third example of the particulate matter sensor optionally includes one or more of the first and the second examples, and further includes wherein the second element further comprises a non-perforated region, the non-perforated region different from the perforated region and wherein the non-perforated region is coaxial to the perforated region and is smaller in diameter than the perforated region. A fourth example of the particulate matter sensor optionally includes one or more of the first through the third examples, and further includes wherein the non-perforated region comprises an inlet configured to allow an exhaust gas to enter the sensor and flow from the non-perforated region towards the perforated region and out into the gap via the plurality of perforations. A fifth example of the particulate matter sensor optionally includes one or more of the first through the fourth examples, and further includes a controller with computer readable instructions stored on non-transitory memory for accumulating particulates in the exhaust gas in the gap by applying a positive voltage to the positive electrodes and a negative voltage to the negative electrodes, determining a load on the sensor based on a current generated between the positive electrodes and the negative electrodes, and responsive to the load being higher than a first threshold, regenerate the sensor by applying a voltage to the heating elements until the soot load is lower than a second threshold, the second threshold being lower than the first threshold. A sixth example of the particulate matter sensor optionally includes one or more of the first through the fifth examples, and further includes wherein the first element comprises outlet holes configured to allow the exhaust gas to exit the sensor.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A particulate matter sensor, comprising:
an outer, non-perforated tube with a plurality of negative electrodes along an inner surface;
a central, perforated element with a plurality of positive electrodes along an outer surface of the central element, the central element positioned within the outer tube; and
an inner tube appended to the central element, each of the outer tube, the central element, and the inner tube having a common axis.

2. The particulate matter sensor of claim 1, wherein the central element comprises a regeneration circuit coupled to an inner surface of the central element for heating the central element, and wherein the central element comprises a plurality of perforations, the plurality of perforations extending through each of the outer surface and the inner surface of the central element.

3. The particulate matter sensor of claim 1, wherein a diameter of the inner tube is smaller than each of a diameter of the outer tube and a diameter of the central element.

4. The particulate matter sensor of claim 2, wherein the plurality of positive electrodes faces the plurality of negative electrodes and is separated from the plurality of negative electrodes by a gap.

5. The particulate matter sensor of claim 2, wherein the plurality of negative electrodes is distributed along the inner surface of the outer tube at a first spacing, and wherein the plurality of positive electrodes is distributed along the outer surface of the central element at a second spacing, the plurality of perforations of the central element interspersed between the plurality of positive electrodes.

6. The particulate matter sensor of claim 5, wherein the first spacing is substantially equal to the second spacing.

7. The particulate matter sensor of claim 5, wherein the first spacing is different from the second spacing.

8. The particulate matter sensor of claim 4, wherein the inner tube comprises a first region and a second region, and wherein the first region is positioned within the outer tube, and the second region extends out of the outer tube into an exhaust pipe, the central element being appended to the inner tube at the first region of the inner tube.

9. The particulate matter sensor of claim 8, wherein the second region comprises an inlet configured to allow exhaust gas in the exhaust pipe to enter the particulate matter sensor via the inlet in a direction opposite to a direction of exhaust flow in the exhaust pipe and flow from the second region towards each of the first region, the central element, and the gap, the exhaust gas flowing from the central element to the gap through the plurality of perforations.

10. The particulate matter sensor of claim 9, wherein the outer tube includes outlet holes configured to direct the exhaust gas from the particulate matter sensor into the exhaust pipe in a direction orthogonal to each of the direction of exhaust flow in the exhaust pipe and to a direction of entry of the exhaust gas into the particulate matter sensor via the inlet.

11. A method, comprising:
streaming a portion of exhaust gas from downstream of a particulate filter into a sensor via an inlet of an inner tube in a direction opposite to flow of exhaust gas in an exhaust pipe;
directing the portion of the exhaust gas towards a space between a sensor positive electrode and a sensor negative electrode through a plurality of perforations of the inner tube, the plurality of perforations located distal to the inlet of the inner tube;

accumulating particulates in the portion of the exhaust gas in the space between the sensor positive electrode and the sensor negative electrode; and guiding the portion of the exhaust gas out of the sensor via outlet holes positioned on an outer tube in a direction orthogonal to each of the flow of the exhaust gas in the exhaust pipe and a direction of flow of the portion of the exhaust gas into the sensor via the inlet.

12. The method of claim 11, wherein the sensor positive electrode and the sensor negative electrode comprise a plurality of positive electrodes formed on an outer surface of the inner tube and a plurality of negative electrodes formed on an inner surface of the outer tube, the inner tube positioned within the outer tube and further separated from the outer tube by the space.

13. The method of claim 11, further comprising determining a load on the sensor positive electrode and the sensor negative electrode based on a current generated in the sensor positive electrode and the sensor negative electrode, and further comprising regenerating the sensor positive electrode and the sensor negative electrode by heating electric elements formed on an inner surface of the inner tube when the load on the sensor positive electrode and sensor negative electrode is higher than a threshold load.

14. A particulate matter sensor, comprising:
evenly spaced negative electrodes formed on a first cylindrical element;
evenly spaced positive electrodes formed on a second cylindrical element, the positive electrodes separated from the negative electrodes by a gap and positioned facing the negative electrodes; and
a plurality of heating elements formed on the second element, the positive electrodes and the plurality of heating elements formed on different surfaces of the second element.

15. The sensor of claim 14, wherein the second element is positioned within, and is coaxial to, the first element.

16. The sensor of claim 14, wherein the second element comprises a perforated region, the perforated region comprising the positive electrodes, the plurality of heating elements, and a plurality of perforations, and wherein the positive electrodes are formed on an outer surface of the perforated region, the plurality of heating elements formed on an inner surface of the perforated region, and the plurality of perforations dispersed between the positive electrodes and the plurality of heating elements.

17. The sensor of claim 16, wherein the second element further comprises a non-perforated region, the non-perforated region different from the perforated region and wherein the non-perforated region is coaxial to the perforated region and is smaller in diameter than the perforated region.

18. The sensor of claim 17, wherein the non-perforated region comprises an inlet configured to allow exhaust gas to enter the sensor and flow from the non-perforated region towards the perforated region and out into the gap via the plurality of perforations.

19. The sensor of claim 18, further comprising a controller with computer readable instructions stored on non-transitory memory for:
accumulating particulates in the exhaust gas in the gap by applying a positive voltage to the positive electrodes and a negative voltage to the negative electrodes;
determining a soot load on the sensor based on a current generated between the positive electrodes and the negative electrodes; and
responsive to the soot load being higher than a first threshold,
regenerate the sensor by applying a voltage to the plurality of heating elements until the soot load is lower than a second threshold, the second threshold being lower than the first threshold.

20. The sensor of claim 18, wherein the first element comprises outlet holes configured to allow the exhaust gas to exit the sensor.

* * * * *